United States Patent
Segawa

(10) Patent No.: US 9,668,644 B2
(45) Date of Patent: Jun. 6, 2017

(54) FLOATATION-VOLUME ADEQUACY DETERMINING SYSTEM AND FLOATATION-VOLUME ADEQUACY DETERMINING METHOD

(75) Inventor: Hidetake Segawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 2323 days.

(21) Appl. No.: 12/545,976

(22) Filed: Aug. 24, 2009

(65) Prior Publication Data

US 2010/0061588 A1    Mar. 11, 2010

(30) Foreign Application Priority Data

Sep. 10, 2008 (JP) ................. 2008-231988

(51) Int. Cl.
  *G06K 9/00* (2006.01)
  *A61B 1/04* (2006.01)
  *A61B 1/00* (2006.01)
(52) U.S. Cl.
  CPC ............ *A61B 1/04* (2013.01); *A61B 1/00156* (2013.01); *A61B 1/00158* (2013.01); *A61B 1/041* (2013.01)
(58) Field of Classification Search
  CPC ................................ A61B 1/041; A61B 5/065
  See application file for complete search history.

(56) References Cited

U.S. PATENT DOCUMENTS

| 8,303,094 B2 * | 11/2012 | Furukawa et al. ............... 347/85 |
| 2004/0264754 A1 | 12/2004 | Kleen et al. |
| 2007/0221233 A1 * | 9/2007 | Kawano et al. ............... 128/899 |

FOREIGN PATENT DOCUMENTS

| JP | 2003-092500 A | 3/2003 |
| JP | 2004-198175 | 7/2004 |
| JP | 2004-340770 | 12/2004 |
| JP | 2005-509643 A | 4/2005 |
| JP | 2007-516765 A | 6/2007 |
| JP | 2007-175448 | 7/2007 |
| WO | WO 03/037296 A2 | 5/2003 |
| WO | WO2005/060348 A2 | 7/2005 |
| WO | WO 2007/077922 A1 | 7/2007 |
| WO | WO 2009/001666 A1 | 12/2008 |

OTHER PUBLICATIONS

Partial European Search Report dated Dec. 7, 2009.
Decision of a Patent Grant dated Jul. 30, 2013 in Japanese Patent Application No. 2008-231988.

* cited by examiner

*Primary Examiner* — Maroun Kanaan
(74) *Attorney, Agent, or Firm* — Scully, Scott, Murphy & Presser, P.C.

(57) ABSTRACT

A floatation-volume adequacy determining system including a receiving unit; an image processing unit; an adequacy determining unit; and a display unit. The receiving unit receives an actual image that is taken by a capsule medical apparatus that is floating in a liquid in the direction toward the liquid level. The image processing unit generates a determination reference image that represents an adequate range of a floatation volume of the capsule medical apparatus adjusted to the actual image that is taken by the capsule medical apparatus. An adequacy determining unit compares the determination reference image and the actual image with each other and determines whether the floatation volume of the capsule medical apparatus is adequate. The display unit displays a result of determining whether the floatation volume of the capsule medical apparatus is adequate.

24 Claims, 12 Drawing Sheets

FLOATATION-VOLUME ADEQUACY DETERMINING SYSTEM AND FLOATATION-VOLUME ADEQUACY DETERMINING METHOD

CROSS-REFERENCE TO RELATED APPLICATION

This application is based upon and claims the benefit of priority from Japanese Patent Application No. 2008-231988, filed on Sep. 10, 2008, the entire contents of which are incorporated herein by reference.

BACKGROUND OF THE INVENTION

1. Field of the Invention

The present invention relates to a system and a method used to determine whether a floatation volume of a capsule medical apparatus that is floating in liquid is adequate.

2. Description of the Related Art

Capsule medical apparatuses that have image-taking and wireless-communication functions are commonly used in the field of endoscopy. A capsule medical apparatus is inserted into a subject, such as a patient, from the mouth in order to observe the interior of the internal organs of the subject. The capsule medical apparatus in the subject sequentially takes in-vivo images of the internal organs (hereinafter, sometimes referred to as "in-vivo images") at predetermined intervals while moving through the internal organs by peristalsis. The capsule medical apparatus sequentially transmits the in-vivo images to the outside. The capsule medical apparatus repeatedly takes and wirelessly transmits in-vivo images over a period of time until it is excreted by the subject.

A group of in-vivo images that are taken by the capsule medical apparatus is received by a receiving device outside the subject and stored in a portable recording medium in the receiving device. The portable recording medium that stores therein the in-vivo images of the subject is detached from the receiving device and then attached to an image display device. The image display device loads the group of in-vivo images from the portable recording medium and displays each of the loaded images on its display. A health professional, such as a doctor or a nurse, observes the interior of the internal organs of the subject by observing each in-vivo image that is displayed on the image display device. Based on the observation result, the health professional can diagnose the subject.

Such capsule medical apparatuses include a capsule medical apparatus whose specific gravity relative to a liquid, such as water, is set lower than 1, and that sequentially takes in-vivo images of a subject while floating in the liquid that is introduced into the internal organs of a subject (see Japanese Patent Application Laid-open No. 2007-175448).

When the floatation volume of a capsule medical apparatus in liquid (i.e., the amount of protrusion of the capsule medical apparatus above the level of the liquid to the atmosphere) changes, the state where in-vivo images are taken by the capsule medical apparatus that is floating also changes depending on the change in the floatation volume in the liquid. In this case, the state where the interior of the subject is observed by observing in-vivo images may be altered unintentionally. Therefore, it is desirable that the floatation volume of the capsule medical apparatus in the liquid be in a predetermined range to ensure a stable state where in-vivo images are taken (i.e., the state where the interior of the subject is observed).

SUMMARY OF THE INVENTION

A floatation-volume adequacy determining system according to an aspect of the present invention includes: an image acquiring unit that acquires an actual image about a capsule medical apparatus that is floating in a liquid; an image processing unit that generates a determination reference image that represents an adequate range of a floatation volume of the capsule medical apparatus; an adequacy determining unit that compares the determination reference image and the actual image with each other and determines whether the floatation volume of the capsule medical apparatus is adequate; and an output unit that outputs a result of determination of whether the floatation volume of the capsule medical apparatus is adequate by the adequacy determining unit.

A floatation-volume adequacy determining system according to another aspect of the present invention includes: an image acquiring unit that acquires an actual image about a capsule medical apparatus that is floating in a liquid; a display unit that displays the actual image; and a control unit that sets an adequate range of a floatation volume of the capsule medical apparatus adjusted to a display scale of the display unit and causes the display unit to display the adequate range and the actual image such that the adequate range is superimposed on the actual image.

A floatation-volume adequacy determining method according to still another aspect of the present invention includes: acquiring an actual image about a capsule medical apparatus that is floating in a liquid; setting an adequate range of a floatation volume of the capsule medical apparatus; determining whether the floatation volume of the capsule medical apparatus is adequate based on the actual image and the adequate range; and outputting a result of determining whether the floatation volume of the capsule medical apparatus is adequate at the determining.

A floatation-volume adequacy determining method according to still another aspect of the present invention includes: acquiring an actual image about a capsule medical apparatus that is floating in a liquid; setting an adequate range of a floatation volume of the capsule medical apparatus; and displaying an image in which the adequate range is superimposed on the actual image.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of a floatation-volume adequacy determining system and a floatation-volume adequacy determining method according to the present invention are described in detail below with reference to the accompanying drawings. A floatation-volume adequacy determining system and a floatation-volume adequacy determining method used to determine whether a floatation volume of a capsule medical apparatus to be examined in liquid is adequate are exemplarily described below. The embodiments do not limit the present invention.

Figure 1:
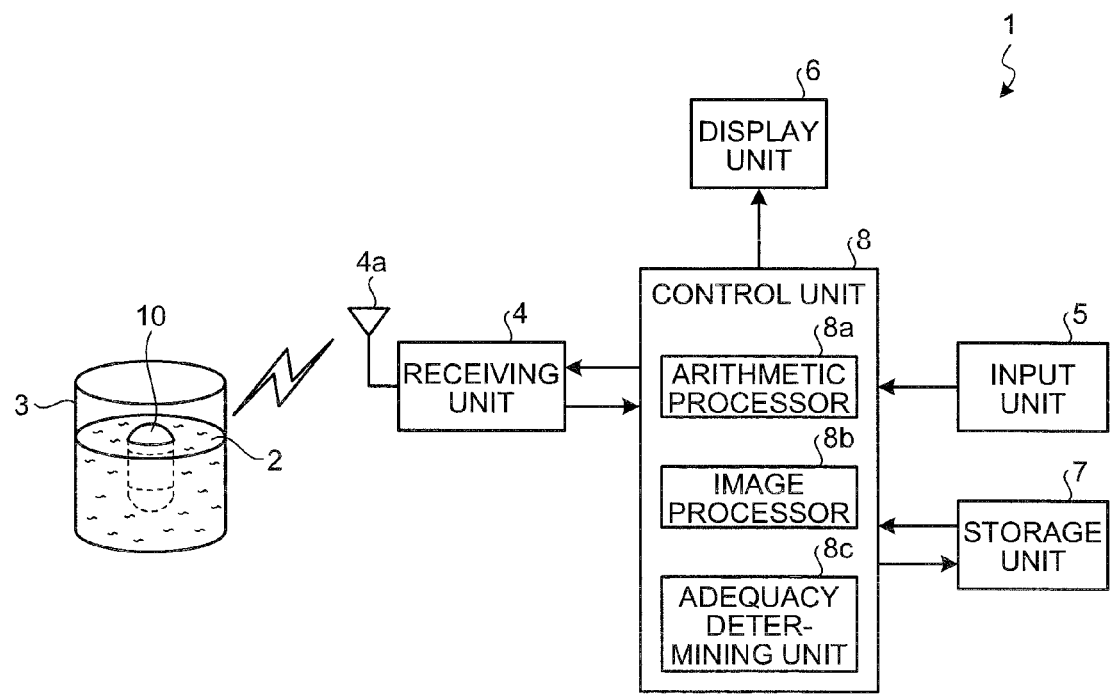
FIG. 1 is a schematic block diagram showing a configuration example of a floatation-volume adequacy determining system according to a first embodiment of the present invention.
Figure 2:
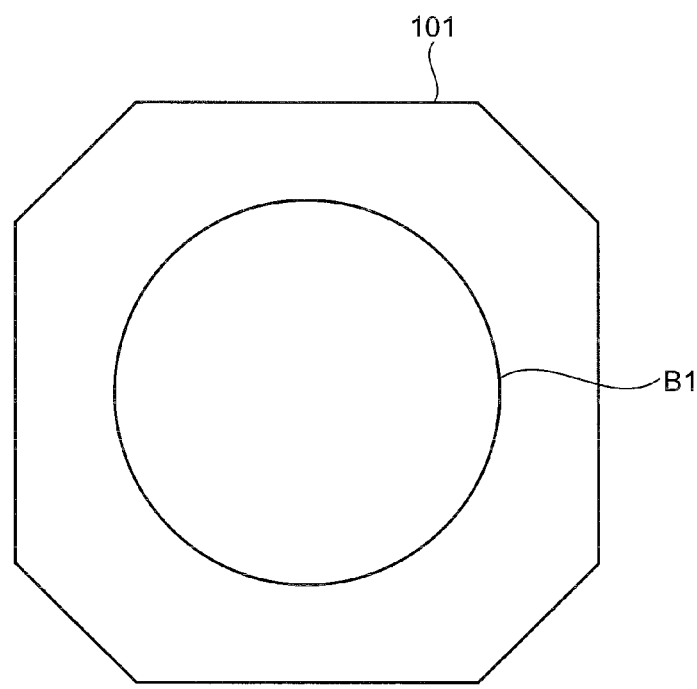
FIG. 2 is a schematic diagram showing an example of an actual image taken by a capsule medical apparatus to be examined while it is floating in liquid.

FIG. 1 is a schematic block diagram showing a configuration example of a floatation-volume adequacy determining system according to a first embodiment of the present invention. FIG. 2 is a schematic diagram showing an example of an actual image that is taken by a capsule medical apparatus to be examined while it is floating in liquid. As represented in FIG. 1, a floatation-volume adequacy determining system 1 according to the first embodiment includes a container 3 in which a capsule medical apparatus 10 to be examined and liquid 2 are stored; a receiving unit 4 that receives an image signal from the capsule medical apparatus 10 in the container 3; an input unit 5 that input various types of information; a display unit 6 that displays a result of determining whether the floatation volume of the capsule medical apparatus 10 is adequate; a storage unit 7 that stores therein various types of information; and a control unit 8 that controls each unit of the floatation-volume adequacy determining system 1.

The container 3 is used to float the capsule medical apparatus 10 in the liquid 2. Specifically, the container 3 is hollow and has an inner diameter larger than the outer diameter of the capsule medical apparatus 10 and a depth larger than the length of the capsule medical apparatus 10 in its longitudinal direction. The capsule medical apparatus 10 to be examined and the liquid 2 in an appropriate amount are introduced into the container 3.

The liquid 2 has a density larger than that of the capsule medical apparatus 10. The liquid 2 is, for example, a liquid that is harmless to human bodies, such as water or normal saline for floating the capsule medical apparatus 10 in the internal organs of the subject. The capsule medical apparatus 10 is an apparatus that is inserted into the internal organs of the subject, and has image-taking and wireless-communication functions. The density of the capsule medical apparatus 10 is smaller than that of the liquid 2. The center of gravity of the capsule medical apparatus 10 is set such that the capsule medical apparatus 10 takes a certain floating posture in the liquid 2. The capsule medical apparatus 10 floats in the liquid 2 in the container 3 and erects near the level of the liquid 2 (i.e., in a posture such that the longitudinal axis of the capsule medical apparatus 10 and the vertical direction are approximately parallel to each other), for example, as represented in FIG. 1.

The container 3 may be cylindrical as represented in FIG. 1 or in a desirable shape, such as rectangular shape. The container 3 may be transparent or semi-transparent. It is preferable that the container 3 be transparent such that the capsule medical apparatus 10 that is floating in the liquid can be visually confirmed from the outside easily. The liquid 2 may be transparent and colorless. However, it is preferable that the liquid 2 be colored such that it can be more easily determined whether the floatation volume of the capsule medical apparatus 10 is adequate.

The receiving unit 4 functions as an image acquiring unit that acquires an actual image of the capsule medical apparatus 10 that is floating in the liquid 2 in the container 3. Specifically, the receiving unit 4 includes an antenna 4a for wireless communications with the capsule medical apparatus 10. The receiving unit 4 receives a wireless signal from the capsule medical apparatus 10 through the antenna 4a. The receiving unit 4 performs a predetermined communication process, such as a decoding process, on the received wireless signal and extracts an image signal from the wireless signal. The image signal contains an actual image about the capsule medical apparatus 10 that is floating in the liquid 2, specifically, data of an actual image 101 that is taken by the capsule medical apparatus 10 as represented in FIG. 2. The receiving unit 4 receives the image signal of the actual image 101 from the capsule medical apparatus 10 as described above and transmits the image signal to the control unit 8.

The actual image 101 is an image taken in the upward vertical direction by the capsule medical apparatus 10 that is floating in the liquid 2. As represented in FIG. 2, the actual image 101 includes as an object a boundary portion B1 between the level of the liquid 2 and the exterior of the capsule medical apparatus 10. When the capsule medical apparatus 10 that is floating in the liquid 2 erects as described above, the boundary portion B1 is circular as represented in FIG. 2. The radius of the boundary portion B1 increases or decreases depending on the floatation volume of the capsule medical apparatus 10 in the liquid 2, i.e., depending on the amount of protrusion of the capsule medical apparatus 10 from the level of the liquid 2. Specifically, the radius of the boundary portion B1 increases with an increase in the protrusion amount of the capsule medical apparatus 10 or decreases with a decrease in the protrusion amount of the capsule medical apparatus 10. When the liquid 2 is a colored liquid, the boundary portion B1 in the actual image 101 is clearly represented. In contrast, when the capsule medical apparatus 10 excessively floats up from the liquid level of the liquid 2 or sinks below the level of the liquid 2 completely, the boundary portion B1 may not be included in the actual image 101.

The input unit 5 includes input devices, such as a mouse and a keyboard. The input unit 5 inputs various types of information to the control unit 8 in response to input operations by a user. Specifically, the input unit 5 inputs instruction information for instructing the control unit 8 and physical information about the capsule medical apparatus 10 to be examined. The physical information about the capsule medical apparatus 10, which is input by the input unit 5, includes a design value (size and mass) of internal members of the capsule medical apparatus 10 and the tolerance thereof; a design value (size and mass) of external members of the capsule medical apparatus 10 and the tolerance thereof; a defined value of an amount of material, such as adhesive, that is used (applied) in manufacturing of the capsule medical apparatus 10 and the tolerance thereof; and a tolerance of the connection difference size of the external members of the capsule medical apparatus 10 in the longitudinal direction.

The display unit 6 functions as an output unit that outputs a result of determining whether the floatation volume of the capsule medical apparatus 10 in the liquid 2 is adequate. Specifically, the display unit 6 is a display device, such as a CRT display or a liquid crystal display. The display unit 6 displays various types of information, which are instructed to display, under the control of the control unit 8. Under the control of the control unit 8, the display unit 6 appropriately displays information that is input by the input unit 5, the actual image 101 taken by the capsule medical apparatus 10 that is received by the receiving unit 4, information that represents a result of determining whether the floatation volume of the capsule medical apparatus 10 in the liquid 2 is adequate, and image information with which it can be determined whether the floatation volume of the capsule medical apparatus 10 in the liquid 2 is adequate.

The storage unit 7 may be constructed with a use of various types of storage media, such as a RAM, an EEPROM, a flash memory, and a hard disk, that store information such that the information is rewritable. The storage unit 7 stores various types of information about which the control unit 8 issues a storing instruction, and transmits information from the various types of information about which the control unit 8 issues a reading instruction. Under the control of the control unit 8, the storage unit 7 appropriately stores or updates the physical information about the capsule medical apparatus 10, which is input by the input unit 5; the actual image 101 that is taken by the capsule medical apparatus 10 and is received by the receiving unit 4; information that represents a reference for determining whether the floatation volume of the capsule medical apparatus 10 is adequate; and information that represents a result of determining whether the floatation volume of the capsule medical apparatus 10 is adequate.

The control unit 8 controls operations of the receiving unit 4, the input unit 5, the display unit 6, and the storage unit 7 that construct the floatation-volume adequacy determining system 1, and controls signal input/output between the units. Specifically, the control unit 8 acquires information input by the input unit 5, such as the physical information about the capsule medical apparatus 10. Based on instruction information that is input by the input unit 5, the control unit 8 controls a receiving operation of the receiving unit 4, a display operation of the display unit 6, and a storing operation of the storage unit 7. The control unit 8 stores in the storage unit 7 various types of information, such as the information that is received by the receiving unit 4 and the information that is input by the input unit 5, or displays them on the display unit 6. The control unit 8 reads the various types of information that is stored in the storage unit 7 as required.

The control unit 8 includes an arithmetic processor 8a that calculates various types of information that are necessary to determine whether the floatation volume of the capsule medical apparatus 10 is adequate; an image processor 8b that performs a process of generating an image; and an adequacy determining unit 8c that determines whether the floatation volume of the capsule medical apparatus 10 is adequate.

Based on the physical information about the capsule medical apparatus 10, which is input by the input unit 5, the arithmetic processor 8a calculates various types of information necessary to determine whether the floatation volume of the capsule medical apparatus 10 is adequate. Specifically, the arithmetic processor 8a calculates, as the various types of information necessary to determine whether the floatation volume of the capsule medical apparatus 10 floating in the liquid 2 is adequate, an upper limit and a lower limit of a mass $W_{CP}$ and a volume $V_{CP}$ of the capsule medical apparatus 10; an upper limit and a lower limit of a density $\rho_{CP}$ of the capsule medical apparatus 10; an upper limit and a lower limit of a protrusion amount $X_A$ of protrusion of the capsule medical apparatus 10 from the level of the liquid 2; and an upper limit and a lower limit of a radius $r_A$ of the boundary portion B1 between the level of the liquid 2 and the exterior of the capsule medical apparatus 10. The various types of information that are calculated by the arithmetic processor 8a are stored in the storage unit 7 based on the control of the control unit 8 and are appropriately read by the control unit 8.

The image processor 8b performs predetermined image processing on the image signal, which is received by the receiving unit 4 from the capsule medical apparatus 10, and generates the actual image 101 that is taken by the capsule medical apparatus 10 (see FIG. 2). The image processor 8b sets an adequate range CR1 of the floatation volume of the capsule medical apparatus 10 in the liquid 2, and generates a determination reference image that represents the adequate range CR1. The image processor 8b converts the upper and lower limits of the radius $r_A$ of the boundary portion B1, which is calculated by the arithmetic processor 8a, to pixels that are displayed by the display unit 6 (i.e., display scale) and sets, as the adequate range CR1 of the floatation volume, a pixel area between the upper and lower limits of the radius $r_A$ of the boundary portion B1. The actual image 101 that is processed by the image processor 8b or the determination reference image is stored in the storage unit 7 under the control of the control unit 8 and read by the control unit 8 appropriately.

The adequacy determining unit 8c compares with each other the determination reference image, which is generated by the image processor 8b, and the actual image 101, which is taken by the capsule medical apparatus 10. Based on a result of the comparison, the adequacy determining unit 8c determines whether the floatation volume of the capsule medical apparatus 10 in the liquid 2 is adequate. Specifically, the adequacy determining unit 8c compares with each other the adequate range CR1 in the determination reference image and the boundary portion B1 in the actual image 101. When the boundary portion B1 is in the adequate range CR1, the adequacy determining unit 8c determines that the floatation volume of the capsule medical apparatus 10 is within the predetermined range, i.e., is adequate. In contrast, when the boundary portion B1 is out of the adequate range CR1, the adequacy determining unit 8c determines that the floatation volume of the capsule medical apparatus 10 is out of the predetermined range, i.e., inadequate.

Figure 3:
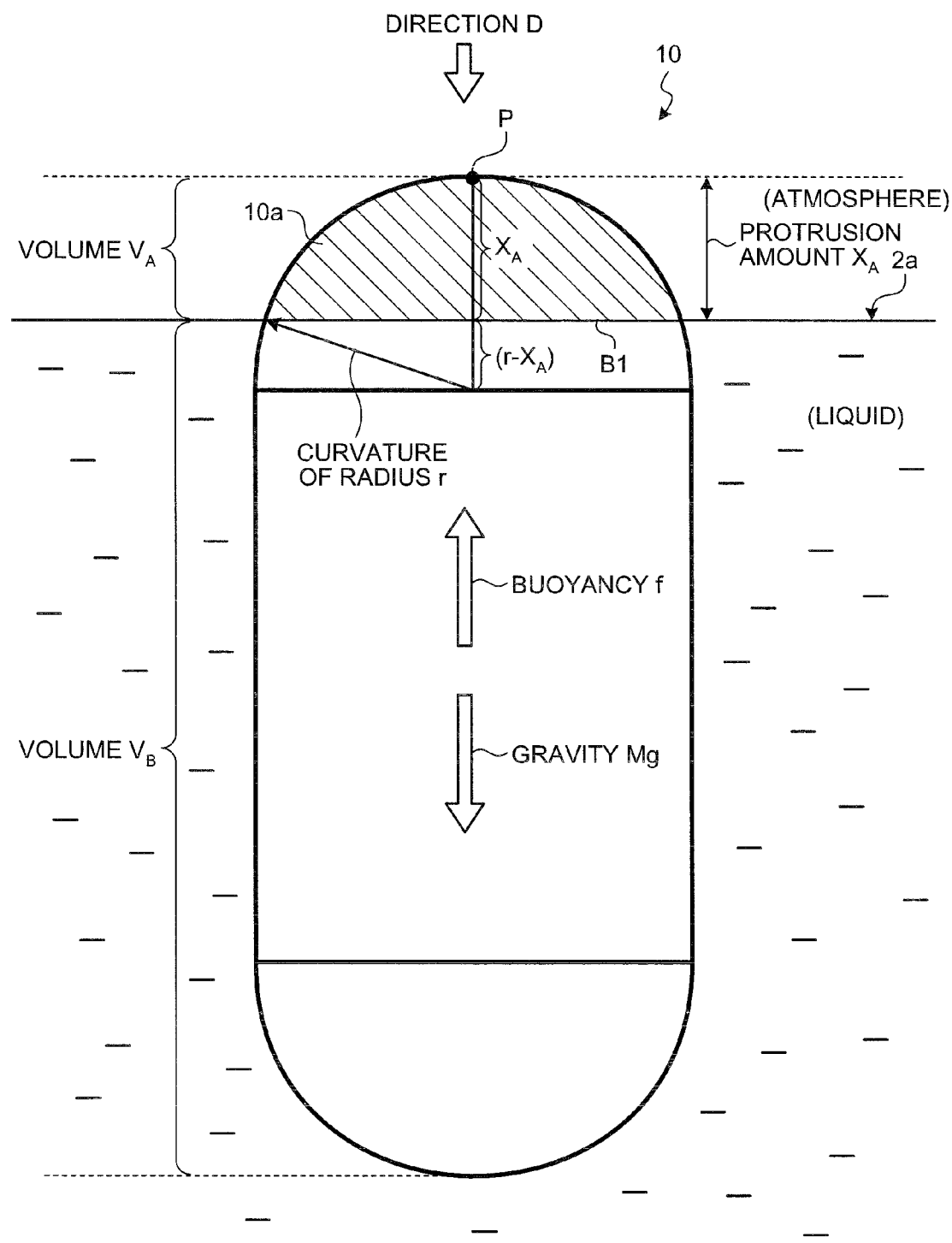
FIG. 3 is a schematic diagram of the capsule medical apparatus that is floating in liquid.
Figure 4:
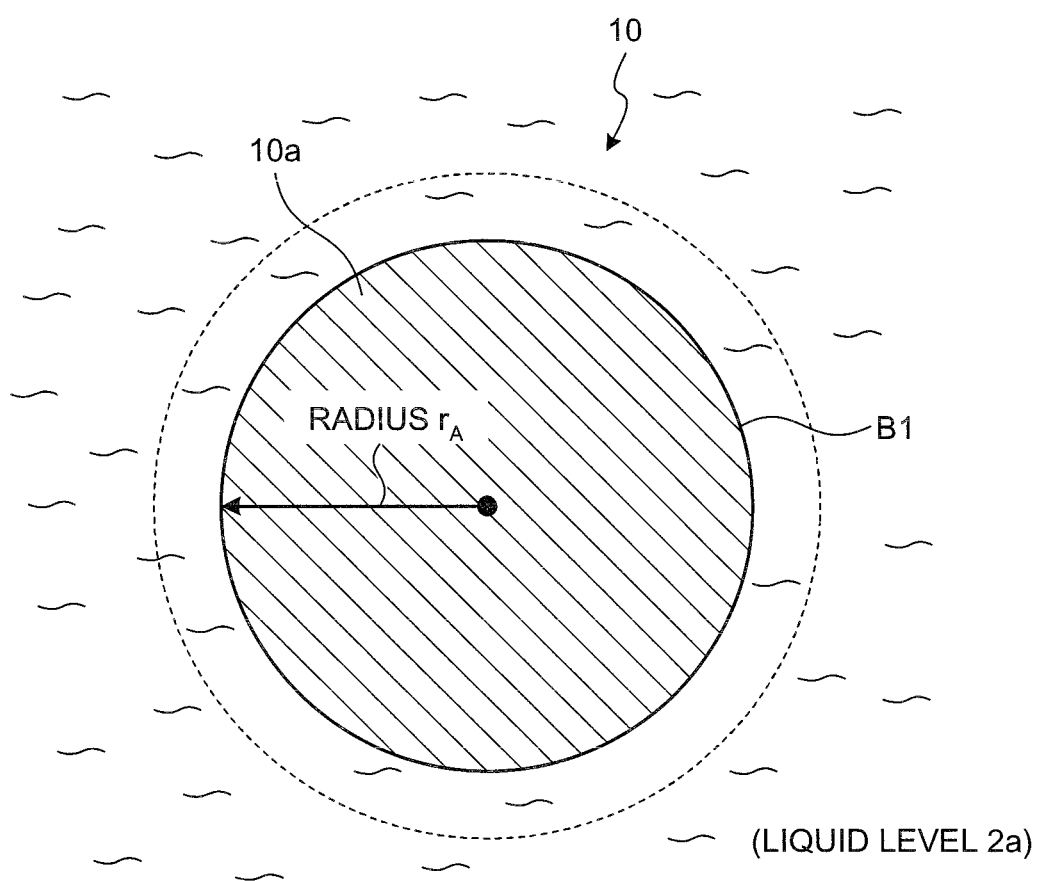
FIG. 4 is a schematic diagram of the capsule medical apparatus when viewed in the direction D represented in FIG. 3.
Figure 5:
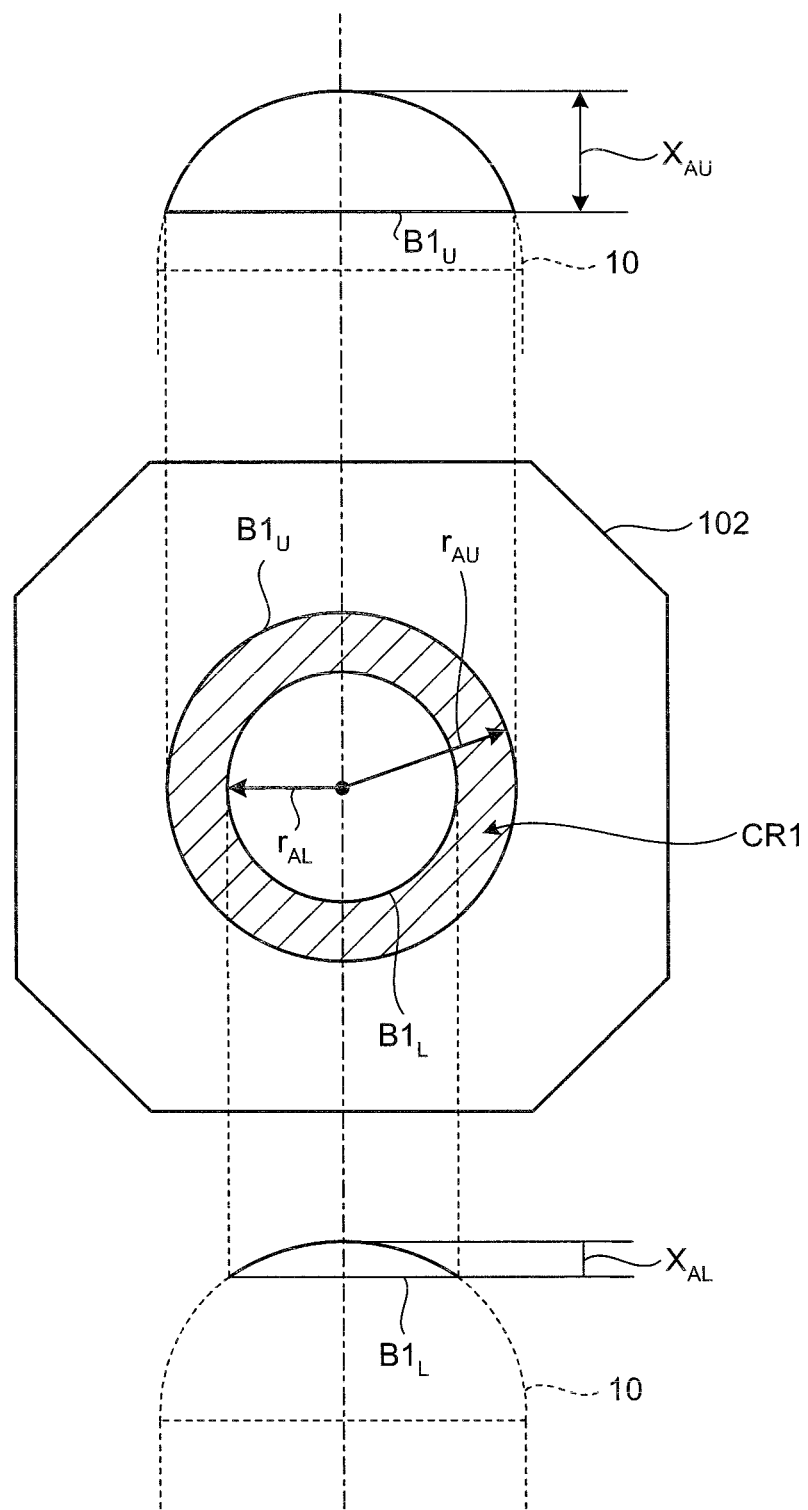
FIG. 5 is a schematic diagram explaining setting of an adequate range of a floatation volume of the capsule medical apparatus in liquid.

Setting of the adequate range CR1 of the floatation volume of the capsule medical apparatus 10 is described in detail below. FIG. 3 is a schematic diagram of the capsule medical apparatus that is floating in liquid. FIG. 4 is a schematic diagram of the capsule medical apparatus when viewed in the direction D represented in FIG. 3. FIG. 5 is a schematic diagram explaining setting of the adequate range of the floatation volume of the capsule medical apparatus in the liquid. FIG. 3 represents the capsule medical apparatus 10 floating in the liquid 2 in the container 3, when viewed in a lateral direction. FIG. 4 represents the capsule medical apparatus 10 floating in the liquid 2 in the container 3, which is viewed from above.

When the capsule medical apparatus 10 to be examined is floating in the liquid 2 in the container 3, a gravity Mg that is applied to the capsule medical apparatus 10 is proportional to a buoyancy f that the capsule medical apparatus 10 receives from the liquid 2, i.e., the gravity Mg equals to the buoyancy f. The gravity Mg is calculated by multiplying the density $\rho_{CP}$ and the volume $V_{CP}$ of the capsule medical apparatus 10. The buoyancy f is calculated by multiplying a density $\rho_{Liq}$ of the liquid 2 that causes the capsule medical apparatus 10 to flow and a volume $V_B$ of a portion of the capsule medical apparatus 10 that sinks below a liquid level 2a of the liquid 2. Therefore, the following Equation (1) is satisfied.

$$\rho_{CP}/\rho_{Liq} = V_B/V_{CP} \tag{1}$$

The left-hand member ($\rho_{CP}/\rho_{Liq}$) is a specific gravity of the capsule medical apparatus 10 relative to the liquid 2.

A volume $V_A$ of a protruding portion 10a of the capsule medical apparatus 10 (a shaded portion represented in FIGS. 3 and 4) that protrudes from the liquid level 2a of the liquid 2 is calculated by subtracting the volume $V_B$ of the portion sinking below the liquid level 2a from the total volume $V_{CP}$ of the capsule medical apparatus 10. In other words, the following Equation (2) is satisfied.

$$V_A = V_{CP} - V_B = V_{CP} - (V_{CP} \times \rho_{CP}/\rho_{Liq}) \tag{2}$$

The volume $V_A$ of the protruding portion 10a can be calculated based on Equation (3).

$$V_A = (1/3) \times \pi \times X_A^2 \times (3 \times r - X_A) \tag{3}$$

In Equation (3), $X_A$ is a protrusion amount and r is a radius of curvature. As represented in FIG. 3, the protrusion amount $X_A$ is a height of the protruding portion 10a from the liquid level 2a to a top P of the protruding portion 10a that is dome-shaped. The height corresponds to the floatation volume of the capsule medical apparatus 10 from the liquid level 2a. In contrast, the radius of curvature r is the radius of curvature of edge portions (dome-shaped casings 11b and 11c to be described below) of the exterior of the capsule medical apparatus 10. The radius of curvature r and the tolerance thereof are input by the input unit 5 as a piece of the physical information about the capsule medical apparatus 10.

The arithmetic processor 8a calculates the upper and lower limits of the volume $V_A$ of the protruding portion 10a of the capsule medical apparatus 10, which protrudes from the liquid level 2a, based on Equations (1) and (2). The arithmetic processor 8a calculates upper and lower limits of the protrusion amount $X_A$ of the capsule medical apparatus 10 from the liquid level 2a from the upper and lower limits of the volume $V_A$ of the protruding portion 10a and based on Equation (3).

The arithmetic processor 8a calculates the upper and lower limits of the radius $r_A$ of the boundary portion B1 between the exterior of the capsule medical apparatus 10 and the liquid level 2a from the upper and lower limits of the protrusion amount $X_A$ and the curvature of radius r. As represented in FIG. 3, the arithmetic processor 8a calculates a difference ($r - X_A$) between the radius of curvature r and the protrusion amount $X_A$, and calculates the upper and lower limits of the curvature of radius $r_A$ of the boundary portion B1 based on the difference ($r - X_A$), the curvature of radius r, and the Pythagorean theorem.

The image processor 8b sets the adequate range CR1 of the floatation volume of the capsule medical apparatus 10 in the liquid 2 based on the upper and lower limits of the radius $r_A$ calculated by the arithmetic processor 8a. Specifically, the image processor 8b converts an upper-limit radius $r_{AU}$ and a lower-limit radius $r_{AL}$ that are the upper and lower limits of the radius $r_A$ calculated by the arithmetic processor 8a to pixels that are displayed by the display unit 6 together with the actual image 101 that is taken by the capsule medical apparatus 10. The image processor 8b then generates a determination reference image 102 that includes an upper-limit boundary portion $B1_U$ whose radius is the upper-limit radius $r_{AU}$ and a lower-limit boundary portion $B1_L$ whose radius is the lower-limit radius $r_{AL}$. The upper-limit boundary portion $B1_U$ and the lower limit boundary portion $B1_L$ are concentric circles in the determination reference image 102 as represented in FIG. 5. The centers of the upper boundary portion $B1_U$ and the lower boundary portion $B1_L$ are set in a predetermined position in the determination reference image 102 (for example, the center of the determination reference image 102).

The upper-limit boundary portion $B1_U$ is an upper limit in a predetermined range of the boundary portion B1 between the exterior of the capsule medical apparatus 10 and the liquid level 2a. The upper-limit boundary portion $B1_U$ corresponds to an upper limit protrusion amount $X_{AU}$ that is the upper limit of the protrusion amount $X_A$ calculated by the arithmetic processor 8a. The lower-limit boundary portion $B1_L$ is the lower limit in the predetermined range of the boundary portion B1 between the exterior of the capsule medical apparatus 10 and the liquid level 2a. The upper-limit boundary portion $B1_L$ corresponds to a lower-limit protrusion amount $X_{AL}$ that is the lower limit of the protrusion amount $X_A$ calculated by the arithmetic processor 8a. As represented by the shaded portion represented in FIG. 5, the image processor 8b sets the pixel area between the upper-limit boundary portion $B1_U$ and the lower-limit boundary portion $B1_L$ as the adequate range CR1 of the floatation volume of the capsule medical apparatus 10 in the liquid 2. The determination reference image 102 that represents the adequate range CR1 is stored in the storage unit 7 under the control of the control unit 8 and read by the control unit 8 appropriately.

Figure 6:
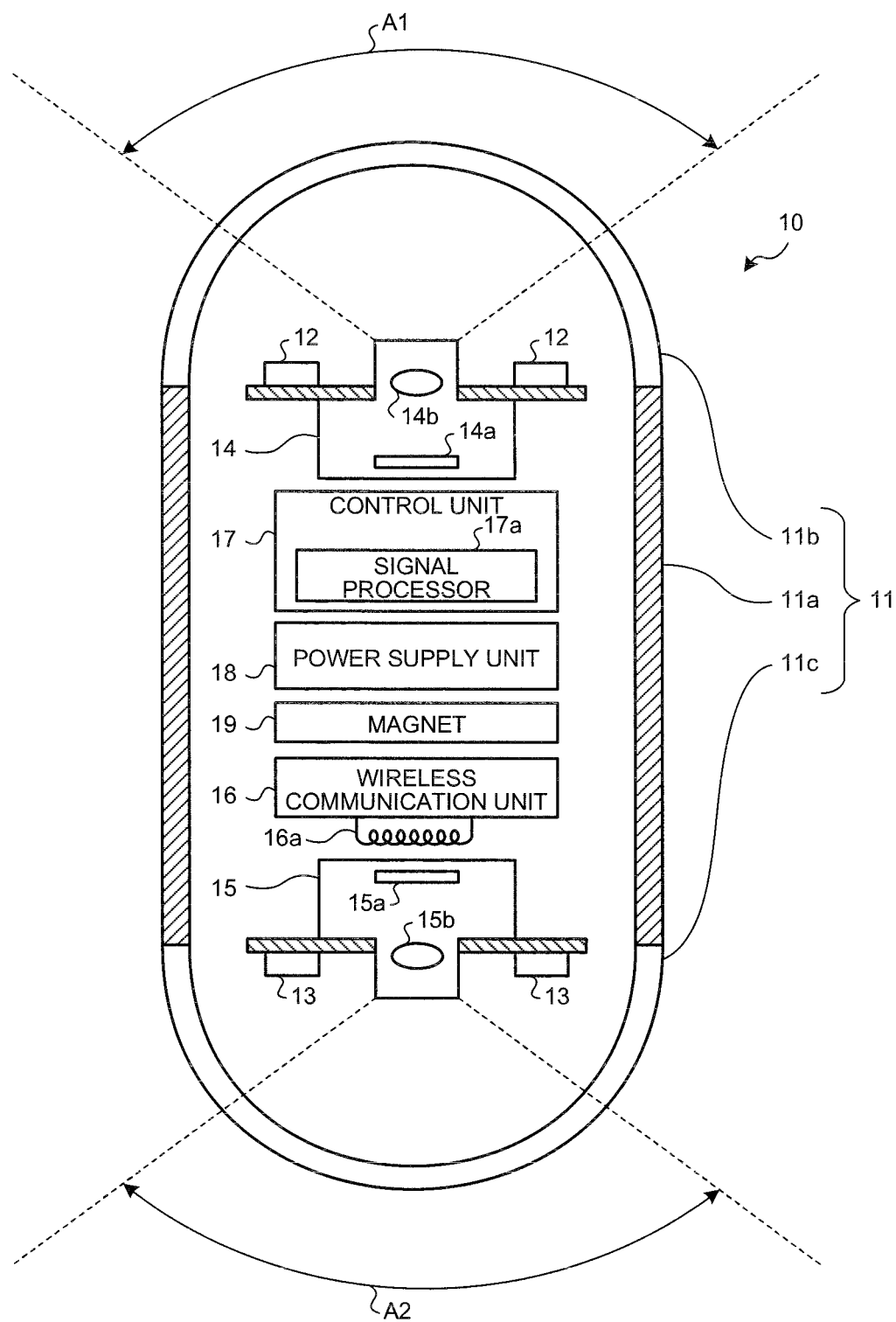
FIG. 6 is a cross-sectional schematic diagram showing a configuration example of the capsule medical apparatus to be examined.

The configuration of the capsule medical apparatus 10 to be examined is described below. FIG. 6 is a cross-sectional schematic diagram showing a configuration example of the capsule medical apparatus to be examined. As represented in FIG. 6, the capsule medical apparatus 10 includes a capsule-shaped casing 11 that is an exterior that is formed in a size such that it can be easily inserted into the internal organs of a subject, such as a patient; illuminating units 12 and 13 that illuminate objects in different directions; and imaging units 14 and 15 that take images of objects in different directions. The capsule medical apparatus 10 further includes a wireless communication unit 16 that wirelessly transmits each image that is taken by the imaging unit 14 or the imaging unit 15; a control unit 17 that controls each unit of the capsule medical apparatus 10; and a power supply unit 18 that supplies electric power to each unit of the capsule medical apparatus 10. The capsule medical apparatus 10 further includes a magnet 19 that moves with a magnetic field that is applied from the outside.

The capsule-shaped casing 11 is an exterior casing that is formed in a size such that it can be inserted into internal organs of a subject, such as a patient. The openings of a cylindrical casing 11a on both ends are closed with the dome-shaped casings 11b and 11c, so that the capsule-shaped casing 11 is formed. The dome-shaped casings 11b and 11c are dome-shaped optical members transparent to lights, such as visible lights, that are emitted by the illuminating units 12 and 13. The cylindrical casing 11a is a colored casing that is not transparent to visible lights. The capsule-shaped casing 11 including the cylindrical casing 11a and the dome-shaped casings 11b and 11c contains the illuminating units 12 and 13, the imaging units 14 and 15, the wireless communication unit 16, the control unit 17, the power supply unit 18, and the magnet 19 in a watertight manner as represented in FIG. 6.

The illuminating units 12 and 13 are constructed with a use of light emitters, such as LEDs, and illuminate image-taking fields A1 and A2 of the imaging units 14 and 15, respectively. Specifically, the illuminating unit 12 emits a light toward the image-taking field A1 of the imaging unit 14 to illuminate an object of the imaging unit 14 through the dome-shaped casing 11b. The illuminating unit 13 emits a light toward the image-taking field A2 of the imaging unit 15 to illuminate an object of the imaging unit 15 through the dome-shaped casing 11c.

The imaging units 14 and 15 take images in different directions. Specifically, the imaging unit 14 includes a solid-state image taking device 14a, such as a CMOS image sensor or a CCD, and an optical system 14b including a lens that forms an image of an object in the image-taking field A1 on a light receiving surface of the solid-state image taking device 14a. The imaging unit 14 takes an image of the object in the image-taking field A1 that is illuminated by the illuminating unit 12. The imaging unit 15 includes a solid-state image taking device 15a, such as a CMOS image sensor or a CCD, and an optical system 15b including a lens that forms an image of an object in the image-taking field A2 on a light receiving surface of the solid-state image taking device 15a. The imaging unit 15 takes an image of the object in the image-taking field A2 that is illuminated by the illuminating unit 13.

When the capsule medical apparatus 10 is a binocular capsule medical apparatus that takes front and back images in the longitudinal direction as represented in FIG. 6, the optical axes of the imaging units 14 and 15 are approximately parallel to or coincide with the long axis that is the center axis of the capsule-shaped casing 11. The image-taking fields A1 and A2 of the imaging units 14 and 15 extend in opposite directions. The actual image 101 (see FIG. 2) containing the boundary portion B1 is taken by any one of the imaging units 14 and 15.

The wireless communication unit 16 includes an antenna 16a. The wireless communication unit 16 wirelessly transmits each image that is taken by the imaging unit 14 or the imaging unit 15 through the antenna 16a sequentially to the outside. Specifically, the wireless communication unit 16 acquires an image signal of an image, which is taken by the imaging unit 14 or the imaging unit 15, from the control unit 17 and performs a modulating process on the acquired image signal to generate a wireless signal. The wireless communication unit 16 transmits the wireless signal to the outside through the antenna 16a.

The control unit 17 controls the illuminating units 12 and 13, the imaging units 14 and 15, and the wireless communication unit 16, and controls input and output of signals between the units. Specifically, the control unit 17 causes the imaging unit 14 to take an image of an object in the image-taking field A1 that is illuminated by the illuminating unit 12, and causes the imaging unit 15 to take an image of an object in the image-taking field A2 that is illuminated by the illuminating unit 13. The control unit 17 causes the wireless communication unit 16 to wirelessly transmit each image, which is taken by the imaging unit 14 or the imaging unit 15, sequentially in the chronological order.

The control unit 17 includes a signal processor 17a. The signal processor 17a acquires image data of the image-taking field A1 from the imaging unit 14. Each time when the signal processor 17a acquires such image data, the signal processor 17a performs predetermined image processing on the image data to generate an image signal that contains the image data of the image-taking field A1. Similarly, the signal processor 17a acquires image data of the image-taking field A2 from the imaging unit 15. Each time when the signal processor 17a acquires such image data, the signal processor 17a performs predetermined image processing on the image data to generate an image signal that contains the image data of the image-taking field A2. Each image signal that is generated by the signal processor 17a is sequentially transmitted to the wireless communication unit 16.

The power supply unit 18 includes a power storage unit, such as a button battery or a capacitor, and a switching unit, such as a magnetic switch. The power supply unit 18 switches on/off the power supply using a magnetic filed that is applied from the outside. When the switch is on, the power supply unit 18 appropriately supplies electric power in the power storage unit to each unit (the illuminating units 12 and 13, the imaging units 14 and 15, the wireless communication unit 16, and the control unit 17) of the capsule medical apparatus 10. When the switch is off, the power supply unit 18 stops the power supply to each unit of the capsule medical apparatus 10.

The magnet 19 is used to guide the capsule medical apparatus 10 with a magnetic field that is applied from the outside. Specifically, the magnet 19 is arranged in a predetermined position in the capsule-shaped casing 11 and forms a magnetic field in a predetermined direction (for example, the direction of the long axis or the radius of the capsule-shaped casing 11). The magnet 19 moves with the magnetic field that is applied from the outside of the capsule-shaped casing 11, and thus the capsule-shaped casing is moved. The capsule-shaped casing 11 takes at least one of a posture changing movement or a displacing movement due to influence of the magnet 19. Alternatively, the capsule-shaped casing 11 remains in a predetermined position due to influence of the magnet 19. If the capsule medical apparatus 10 is not configured to be guided by an eternal magnetic field, it is not required to incorporate the magnet 19.

Figure 7:
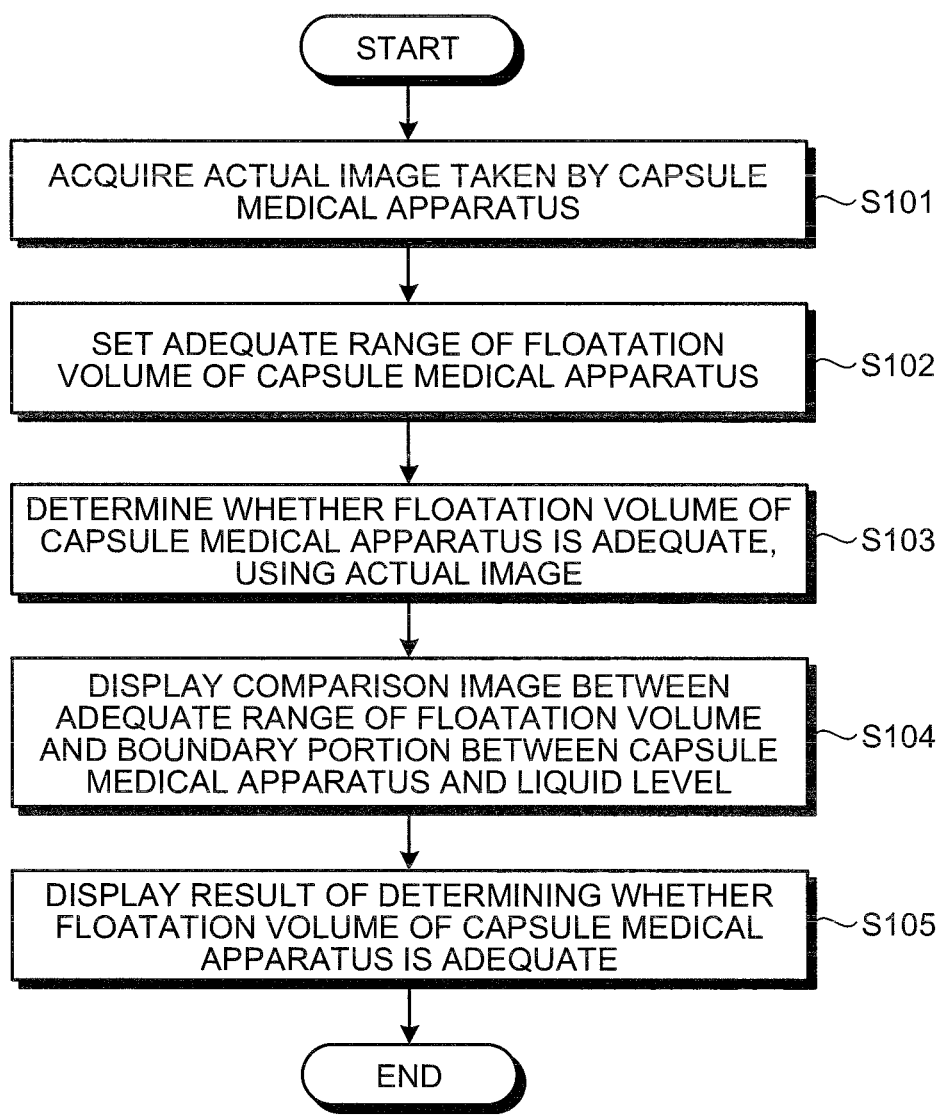
FIG. 7 is an explanatory flowchart showing a procedure of the floatation-volume adequacy determining system according to the first embodiment of the present invention.
Figure 8:
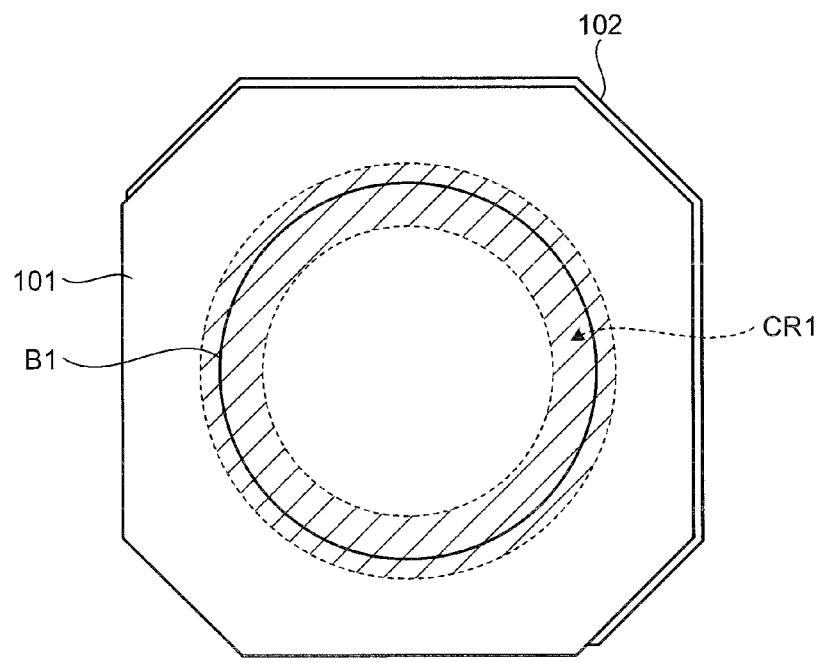
FIG. 8 is a schematic diagram explaining a process of determining a floatation-volume adequacy of the capsule medical apparatus according to the first embodiment of the present invention.
Figure 9:
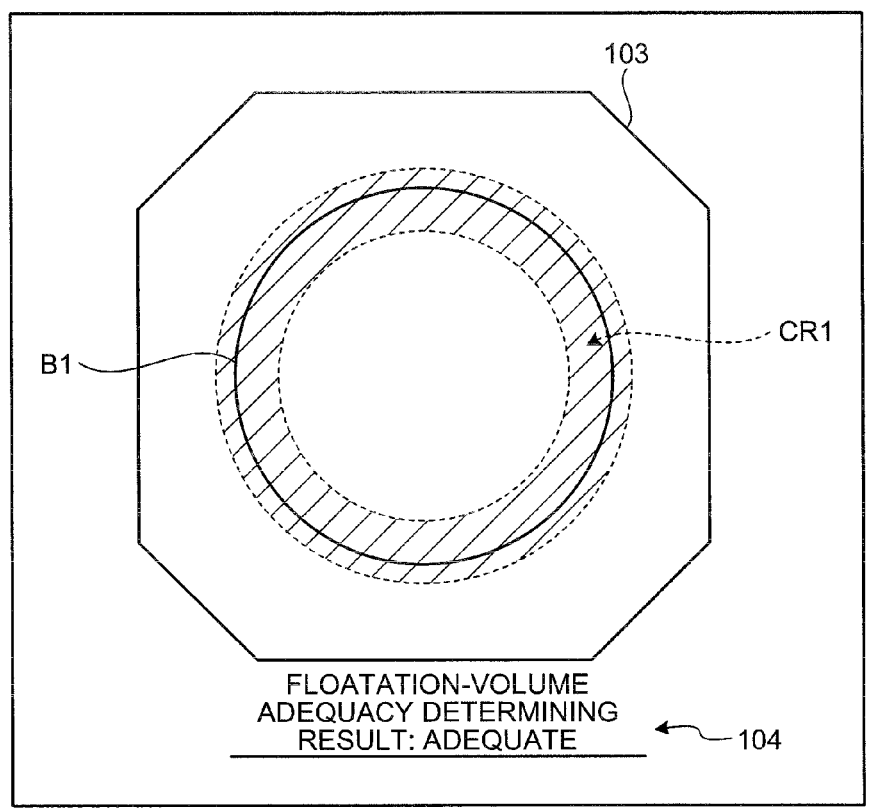
FIG. 9 is a schematic diagram that exemplarily represents the state where a result of determining whether the floatation volume of the capsule medical apparatus is adequate is displayed.

The floatation-volume adequacy determining method and operations of the floatation-volume adequacy determining system 1 according to the first embodiment of the present invention are described below. FIG. 7 is an explanatory flowchart showing a procedure of the floatation-volume adequacy determining system according to the first embodiment of the present invention. FIG. 8 is a schematic diagram explaining a process of determining the floatation volume of the capsule medical apparatus according to the first embodiment of the present invention. FIG. 9 is a schematic diagram that exemplarily represents the state where a result of determining whether the floatation volume of the capsule medical apparatus is adequate is displayed.

In the floatation-volume adequacy determining system 1 according to the first embodiment of the present invention, the physical information about the capsule medical apparatus 10 is previously input to the control unit 8 by the input unit 5 and stored in the storage unit 7 before the procedure represented in FIG. 7 is started. In addition, as a preparation operation, the liquid 2 in an appropriate amount is introduced to the container 3 and the capsule medical apparatus 10 to be examined is put in the liquid 2.

After the preparation operation is completed, the control unit 8 of the floatation-volume adequacy determining system 1 acquires the actual image 101 that is taken by the capsule medical apparatus 10 to be examined (step S101) as represented in FIG. 7. At step S101, the control unit 8 controls the receiving unit 4 to receive the image signal of the actual image 101 from the capsule medical apparatus 10 that is floating in the liquid 2. The control unit 8 acquires the actual image 101 taken by the capsule medical apparatus 10 through the receiving unit 4. The capsule medical apparatus 10 in the liquid 2 starts taking and wirelessly transmitting the actual image 101 based on an application of a magnetic field from a magnet or the like, which switches on the power supply.

The control unit 8 sets the adequate range CR1 of the floatation volume of the capsule medical apparatus 10 in the liquid 2 (step S102).

At step S102, the arithmetic processor 8a calculates the upper-limit protrusion amount $X_{AU}$ and the lower-limit protrusion amount $X_{AL}$ of protrusion of the capsule medical apparatus 10 from the liquid level 2a of the liquid 2 based on the pre-input physical information about the capsule medical apparatus 10 and Equations (1) to (3). Subsequently, from the upper-limit protrusion amount $X_{AU}$, the lower-limit protrusion amount $X_{AL}$, and the radius of curvature r of the dome-shaped casings 11b and 11c of the capsule medical apparatus 10, the arithmetic processor 8a calculates the upper-limit radius $r_{AU}$ and the lower-limit radius $r_{AL}$ of the boundary portion B1 between the exterior of the capsule medical apparatus 10 and the liquid level 2a.

The image processor 8b converts the upper-limit radius $r_{AU}$ and the lower-limit radius $r_{AL}$, which are calculated by the arithmetic processor 8a, to pixels that are displayed by the display unit 6 together with the actual image 101, which is taken by the capsule medical apparatus 10. The image processor 8b sets the upper-limit boundary portion $B1_U$ whose radius is the upper-limit radius $r_{AU}$ and the lower-limit boundary portion $B1_L$ whose radius is the lower-limit radius $r_{AL}$, and sets a pixel area between the upper-limit boundary portion $B1_U$ and the lower-limit boundary portion $B1_L$ as the adequate range CR1 of the floatation volume of the capsule medical apparatus 10 in the liquid 2. The image processor 8b generates the determination reference image 102 that represents the adequate range CR1. The display scale of the determination reference image 102 that is generated by the image processor 8b is equal to the display scale of the actual image 101 taken by the capsule medical apparatus 10.

After the process at step S102 is completed, the control unit 8 determines whether the floatation volume of the capsule medical apparatus 10 in the liquid 2 is adequate, using the actual image 101 (step S103). At step S103, the adequacy determining unit 8c compares with each other the determination reference image 102 that is generated by the image processor 8b and the actual image 101 that is taken by the capsule medical apparatus 10. Based on the result of the comparison, the adequacy determining unit 8c determines whether the floatation volume of the capsule medical apparatus 10 in the liquid 2 is adequate.

Specifically, as represented in FIG. 8, the adequacy determining unit 8c matches the center of the boundary portion B1 of the actual image 101 to the center of the adequate range CR1 of the determination reference image 102, and compares with each other the boundary portion B1 in the actual image 101 and the adequate range CR1 in the determination reference image 102. When the boundary portion B1 is within the adequate range CR1, the adequacy determining unit 8c determines that the floatation volume of the capsule medical apparatus 10 in the liquid 2 is adequate. In contrast, when the boundary portion B1 is out of the adequate range CR1, the adequacy determining unit 8c determines that the floatation volume of the capsule medical apparatus 10 is inadequate. Because the boundary portion B1 is positioned within the adequate range CR1 in FIG. 8, it is determined that the floatation volume of the capsule medical apparatus 10 is adequate.

Thereafter, the control unit 8 causes the display unit 6 to display a comparison image between the adequate range CR1 and the boundary portion B1 between the exterior of the capsule medical apparatus 10 and the liquid level 2a (step S104). At step S104, the control unit 8 causes the display unit 6 to display the adequate range CR1 of the floatation volume, which is set at step S102, and the actual image 101, which is acquired at step S101, such that the adequate range CR1 is superimposed on the actual image 101. Under the control of the control unit 8, the display unit 6 outputs and displays, as represented in FIG. 9, a comparison image 103 with which the boundary portion B1 and the adequate range CR1 of the floatation volume can be visually compared with each other. The comparison image 103 is generated by the image processor 8b by superimposing the actual image 101 on the determination reference image 102.

Subsequently, the control unit 8 causes the display unit 6 to display a result of determination at step S103 on whether the floatation volume of the capsule medical apparatus 10 is adequate (step S105) and completes the process. At step S105, based on the control of the control unit 8 and as represented in FIG. 9, the display unit 6 displays and outputs determination result information 104 that represents a result of determining whether the floatation volume of the capsule medical apparatus 10 in the liquid 2 is adequate. By visually recognizing the determination result information 104 that is displayed on the display unit 6, the user can know whether the floatation volume of the capsule medical apparatus 10 to be examined is adequate (it is adequate in the case of FIG. 9). By visually recognizing the comparison image 103, the user can determine an inadequate state in the case where the floatation volume of the capsule medical apparatus 10 is inadequate in addition to determining whether the capsule medical apparatus 10 is adequate. Specifically, when the boundary portion B1 deviates to an outer side of the adequate range CR1 in the comparison image 103, the user can know that the capsule medical apparatus 10 is inadequate because it floats too much. In contrast, when the boundary portion B1 deviates to an inner side of the adequate range CR1, the user can know that the capsule medical apparatus 10 is inadequate because it sinks too much.

As described above, in the floatation-volume adequacy determining system and the floatation-volume adequacy determining method according to the first embodiment of the present invention, the following is performed. The actual image that is taken by the capsule medical apparatus that is floating in the liquid in the direction toward the liquid level is acquired. The adequate range of the floatation volume of the capsule medical apparatus to be examined is set. The adequate range of the floatation volume and the boundary portion between the exterior of the capsule medical apparatus and the liquid level, which is represented in the actual image, are compared with each other, and it is determined whether the floatation volume of the capsule medical apparatus in the liquid is adequate. The result of determining whether the floatation volume is adequate is displayed. Because of this configuration, the predetermined range of the floatation volume, which is previously determined in consideration for the tolerance of the mass and size of the capsule medical apparatus in manufacturing and design, such as the tolerance of the mass and size of each member of the capsule medical apparatus in manufacturing and design, and the actual floatation volume of the capsule medical apparatus in the liquid after manufacturing or before shipment can be easily compared with each other. As a result, it can be easily determined whether the floatation volume of the capsule medical apparatus that is floating in the liquid is within the predetermined range.

A second embodiment of the present invention is described below. In the first embodiment, the actual image 101 that is taken in the direction toward the liquid level 2a (i.e., in the upper vertical direction) by the capsule medical apparatus 10 floating in the liquid 2 is received through the receiving unit 4. In the second embodiment, an imaging unit that is separate from the capsule medical apparatus 10 takes, from above the capsule medical apparatus 10, an actual image that includes as an object the capsule medical apparatus 10 floating in the liquid 2 and the liquid level 2a.

Figure 10:
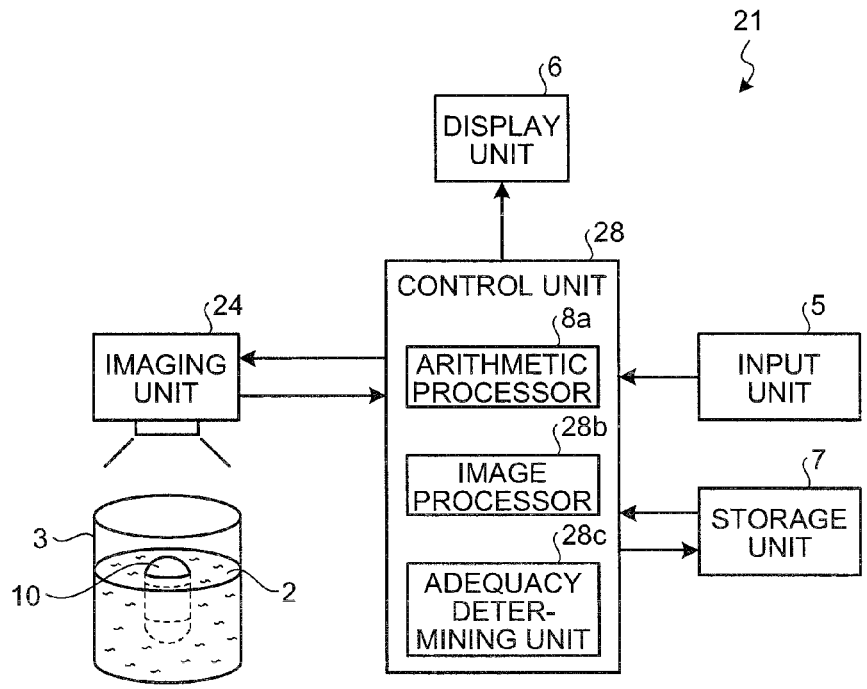
FIG. 10 is a schematic block diagram showing a configuration example of a floatation-volume adequacy determining system according to a second embodiment of the present invention.

FIG. 10 is a schematic block diagram showing a configuration example of a floatation-volume adequacy determining system according to the second embodiment of the present invention. As represented in FIG. 10, a floatation-volume adequacy determining system 21 according to the second embodiment includes an imaging unit 24 instead of the receiving unit 4 of the floatation-volume adequacy determining system 1 according to the first embodiment; and a control unit 28 instead of the control unit 8. Other aspects of the configuration are same as those of the first embodiment, and the same parts are denoted by the same reference numerals.

Figure 11:
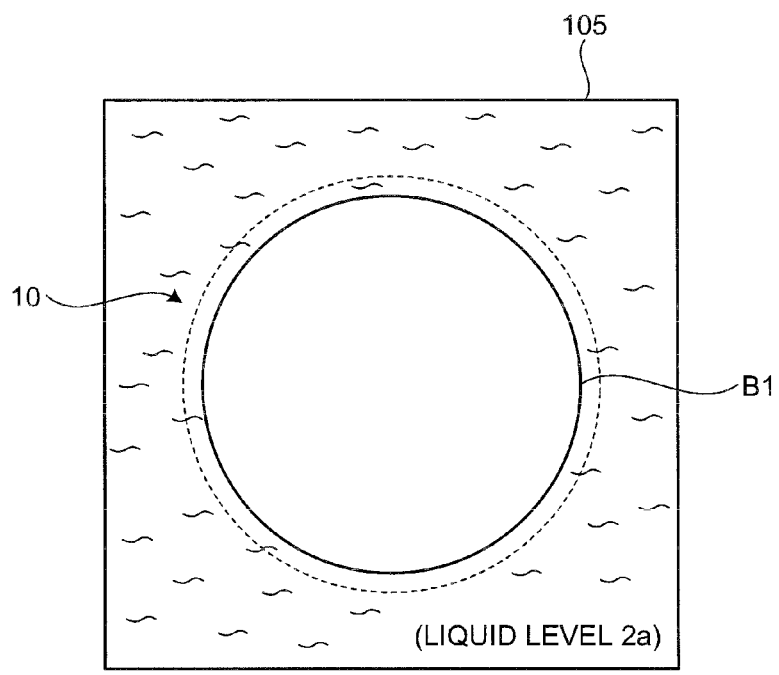
FIG. 11 is a schematic diagram showing an example of an actual image of the capsule medical apparatus that is floating in liquid, which is taken from above.

The imaging unit 24 functions as an image acquiring unit that acquires an actual image about the capsule medical apparatus 10 that is floating in the liquid 2 in the container 3. Specifically, the imaging unit 24 includes a light emitting device, such as an LED; a solid-state image taking device, such as a CMOS or a CCD; and an optical system, such as a focus lens. As represented in FIG. 10, the imaging unit 24 is arranged above the container 3, and takes from above an image of the capsule medical apparatus 10 that is floating in the liquid 2 in the container 3. FIG. 11 is a schematic diagram showing an example of an actual image of the capsule medical apparatus that is floating in the liquid, which is taken from above. The imaging unit 24 takes (acquires) an actual image 105 of the capsule medical apparatus 10 that is floating in the liquid 2 while illuminating the capsule medical apparatus 10 from above. The actual image 105 that is taken by the imaging unit 24 includes as an object the capsule medical apparatus 10 that is floating in the liquid 2, the liquid level 2a of the liquid 2, and the boundary portion B1 between the exterior of the capsule medical apparatus 10 and the liquid level 2a. The imaging unit 24 transmits an image signal of the actual image 105 to the control unit 28.

The control unit 28 has an imaging control function for controlling operations of the imaging unit 24. Specifically, the control unit 28 causes the imaging unit 24 to take the actual image 105 of the capsule medical apparatus 10 in the liquid 2 based on instruction information that is input by the input unit 5, and acquires the image signal of the actual image 105 from the imaging unit 24. The control unit 28 stores in the storage unit 7 or displays on the display unit 6 the actual image 105 of the capsule medical apparatus 10 that is taken by the imaging unit 24 instead of the actual image 101 that is taken by the capsule medical apparatus 10.

The control unit 28 includes an image processor 28b instead of the image processor 8b of the floatation-volume adequacy determining system 1 according to the first embodiment, and an adequacy determining unit 28c instead of the adequacy determining unit 8c. Other functions of the control unit 28 are same as those of the control unit 8 of the floatation-volume adequacy determining system 1 according to the first embodiment.

The image processor 28b performs predetermined image processing on the image signal that is acquired from the imaging unit 24, and generates the actual image 105 (see FIG. 11) of the capsule medical apparatus 10 that is taken by the imaging unit 24. The image processor 28b performs a process approximately same as that of the image processor 8b according to the first embodiment to set an adequate range CR1 of the floatation volume of the capsule medical apparatus 10 in the liquid 2, and generates the determination reference image 102 that represents the adequate range CR1. The image processor 28b sets the adequate range CR1 of the floatation volume that is adjusted to the actual image 105 of the capsule medical apparatus 10 taken by the imaging unit 24 instead of the actual image 101 that is taken by the capsule medical apparatus 10.

The adequacy determining unit 28c is same as the adequacy determining unit 8c of the first embodiment except that the adequacy determining unit 28c uses the actual image 105 of the capsule medical apparatus 10 that is taken by the imaging unit 24 instead of the actual image 101 that is taken by the capsule medical apparatus 10. In other words, the adequacy determining unit 28c compares with each other the actual image 105 of the capsule medical apparatus 10 that is taken by the imaging unit 24 and the determination reference image 102 that is generated by the image processor 28b. Based on the result of the comparison, the adequacy determining unit 28c determines whether the floatation volume of the capsule medical apparatus 10 in the liquid 2 is adequate.

Figure 12:
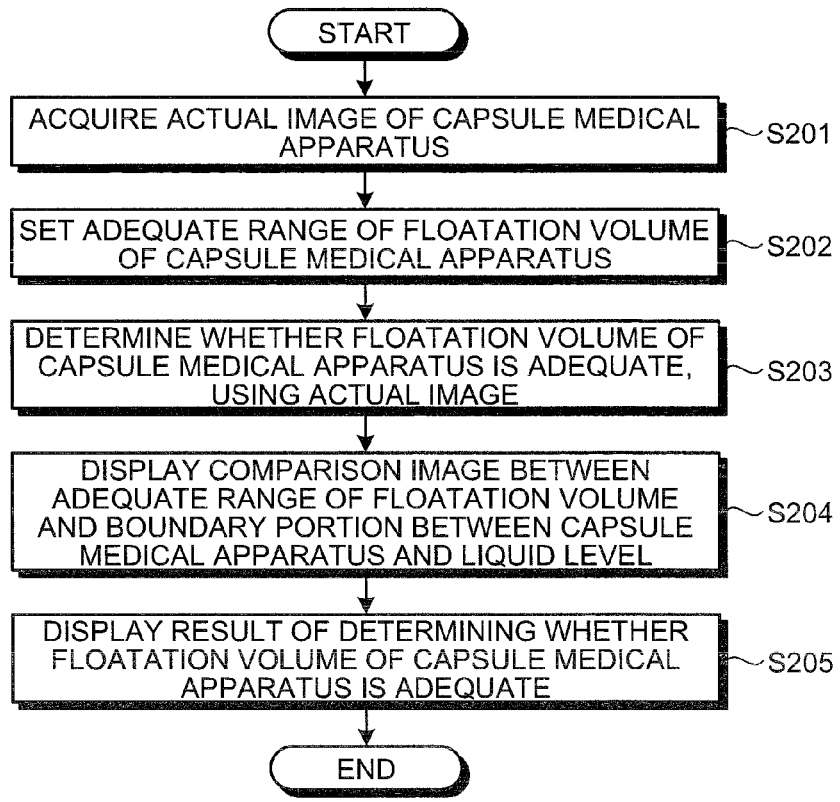
FIG. 12 is an explanatory flowchart showing a procedure of the floatation-volume adequacy determining system according to the second embodiment of the present invention.

The floatation-volume adequacy determining method and operations of the floatation-volume adequacy determining system 21 according to the second embodiment of the present invention are described below. FIG. 12 is an explanatory flowchart showing a procedure of the floatation-volume adequacy determining system according to the second embodiment of the present invention.

In the floatation-volume adequacy determining system 21 according to the second embodiment of the present invention, the physical information about the capsule medical apparatus 10 is previously input to the control unit 28 by the input unit 5 and stored in the storage unit 7 before the procedure represented in FIG. 12 is started. In addition, as a preparation operation, the liquid 2 in an appropriate amount is introduced to the container 3 and the capsule medical apparatus 10 to be examined is put in the liquid 2.

After the preparation operation is completed, the control unit 28 of the floatation-volume adequacy determining system 21 acquires the actual image 105 of the capsule medical apparatus 10 to be examined as represented in FIG. 12 (step S201). At step S201, the control unit 28 controls the imaging unit 24 based on instruction information that is input by the input unit 5. The imaging unit 24 takes from above an image of the capsule medical apparatus 10 in the liquid 2 based on the control of the control unit 28, and transmits an image signal of the actual image 105 of the capsule medical apparatus 10 to the control unit 28. The control unit 28 acquires the actual image 105 of the capsule medical apparatus 10 from the imaging unit 24.

The control unit 28 then sets the adequate range CR1 of the floatation volume of the capsule medical apparatus 10 in the liquid 2 (step S202).

At step S202, the image processor 28b converts an upper-limit radius $r_{AU}$ and a lower-limit radius $r_{AL}$ that are calculated by the arithmetic processor 8a to pixels that are displayed by the display unit 6 and adjusted to the actual image 105 of the capsule medical apparatus 10 that is taken by the imaging unit 24. The image processor 28b then performs the process same as that of the image processor 8b according to the first embodiment to set the adequate range CR1 of the floatation volume of the capsule medical apparatus 10 in the liquid 2 and generate the determination reference image 102 that represents the adequate range CR1. The display scale of the determination reference image 102 that is generated by the image processor 28b is equal to the display scale of the actual image 105 of the capsule medical apparatus 10 that is taken by the imaging unit 24.

The control unit 28 then determines whether the floatation volume of the capsule medical apparatus 10 in the liquid 2 is adequate, using the actual image 105 (step S203). At step S203, the adequacy determining unit 28c compares with each other the determination reference image 102 that is generated by the image processor 28b and the actual image 105 of the capsule medical apparatus 10 that is taken by the imaging unit 24. Based on the result of the comparison, the adequacy determining unit 28c determines whether the floatation volume of the capsule medical apparatus 10 in the liquid 2 is adequate.

Specifically, the adequacy determining unit 28c matches the center of a boundary portion B1 of the actual image 105 to the center of the adequate range CR1 of the determination reference image 102, and compares with each other the boundary portion B1 in the actual image 105 and the adequate range CR1 in the determination reference image 102. When the boundary portion B1 is within the adequate range CR1, the adequacy determining unit 28c determines that the floatation volume of the capsule medical apparatus 10 in the liquid 2 is adequate. In contrast, when the boundary portion B1 is out of the adequate range CR1, the adequacy determining unit 28c determines that the floatation volume of the capsule medical apparatus 10 is inadequate.

Thereafter, the control unit 28 controls the display unit 6 to display a comparison image between the adequate range CR1 and the boundary portion B1 between the exterior of the capsule medical apparatus 10 and the liquid level 2a (step S204). At step S204, the control unit 28 controls the display unit 6 to display the adequate range CR1 of the floatation volume, which is set at step S202, and the actual image 105, which is acquired at step S201, such that the adequate range CR1 is superimposed on the actual image 105. Based on the control of the control unit 28, the display unit 6 outputs and displays, as in the case of the first embodiment, the comparison image 103 with which the boundary portion B1 and the adequate range CR1 of the floatation volume can be visually compared with each other. In the second embodiment, the comparison image 103 is generated by the image processor 28b by superimposing the actual image 105 on the determination reference image 102.

Subsequently, as at step S105 of the first embodiment (see FIG. 7), the control unit 28 controls the display unit 6 to display a result of determination at step S203 of whether the floatation volume of the capsule medical apparatus 10 is adequate (step S205), and completes the process. At step S205, based on the control of the control unit 28, the display unit 6 displays and outputs the determination result information 104 that represents the result of determining whether the floatation volume of the capsule medical apparatus 10 in the liquid 2 is adequate as in the case of the first embodiment (see FIG. 9).

As described above, in the second embodiment of the present invention, the actual image is taken from above that includes the capsule medical apparatus that is floating in the liquid and the liquid level, and the adequate range of the floatation volume of the capsule medical apparatus to be examined is set and adjusted to the actual image. Other aspects of the configuration are same as those of the first embodiment. Therefore, the floatation-volume adequacy determining system and the floatation-volume adequacy determining method can be provided with which it can be easily determined whether the floatation volume of the capsule medical apparatus in the liquid is adequate without consuming the power of the battery incorporated in the capsule medical apparatus while achieving the effects and functions same as those of the first embodiment.

A third embodiment of the present invention is described below. In the second embodiment, the actual image including as an object the capsule medical apparatus 10 floating in the liquid 2 and the liquid level 2a is taken from above the capsule medical apparatus 10. In the third embodiment, an actual image including as an object the capsule medical apparatus 10 floating in the liquid 2 and the liquid level 2a is taken in a lateral direction.

Figure 13:
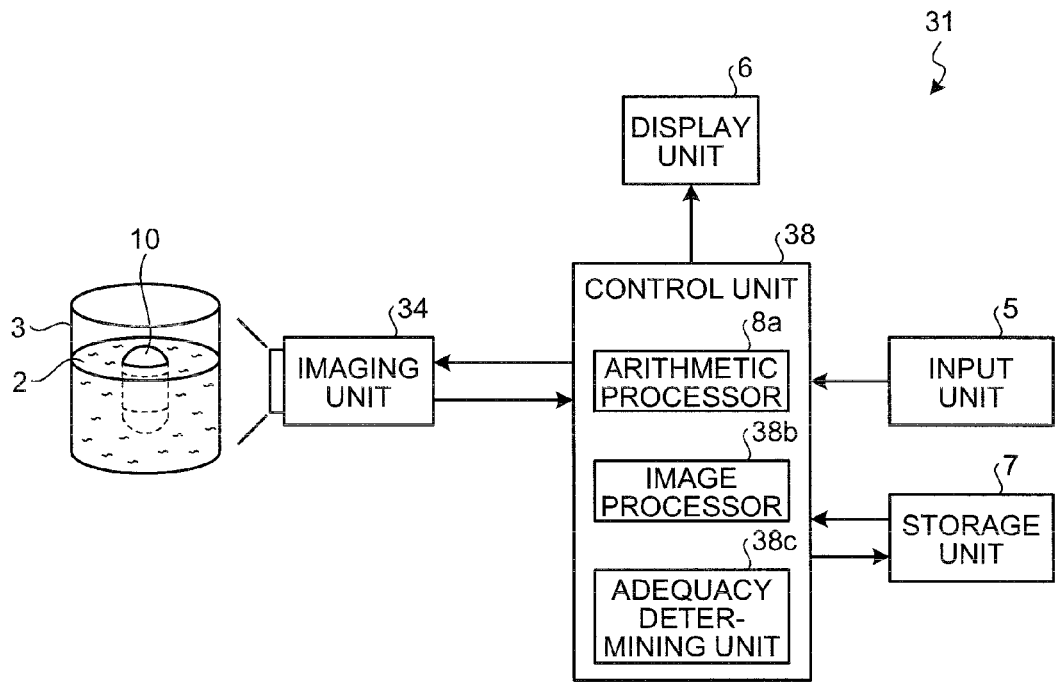
FIG. 13 is a schematic block diagram showing a configuration example of a floatation-volume adequacy determining system according to a third embodiment of the present invention.

FIG. 13 is a schematic block diagram showing an example of a configuration of a floatation-volume adequacy determining system according to a third embodiment of the present invention. As represented in FIG. 13, a floatation-volume adequacy determining system 31 according to the third embodiment includes an imaging unit 34 instead of the imaging unit 24 of the floatation-volume adequacy determining system 21 according to the second embodiment, and a control unit 38 instead of the control unit 28. In the floatation-volume adequacy determining system 31 according to the third embodiment, the container 3 is transparent such that an image of the capsule medical apparatus 10 can be taken in the lateral direction by the imaging unit 34. Other aspects of the configuration are same as those of the second embodiment, and the same parts are denoted by the same reference numerals.

Figure 14:
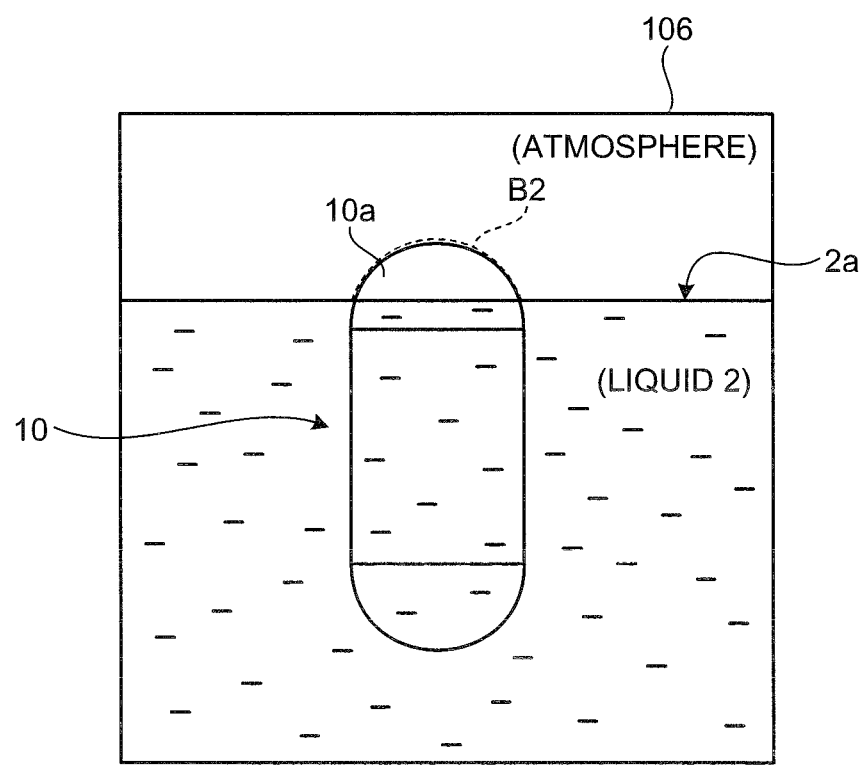
FIG. 14 is a schematic diagram showing an example of an actual image of the capsule medical apparatus that is floating in liquid, which is taken in a lateral direction.

The imaging unit 34 functions as an image acquiring unit that acquires an actual image about the capsule medical apparatus 10 that is floating in the liquid 2 in the container 3. Specifically, the imaging unit 34 includes a light emitting device, such as an LED; a solid-state image taking device, such as a CMOS or a CCD; and an optical system, such as a focus lens. As represented in FIG. 13, the imaging unit 34 is arranged on one side of the container 3, and takes in the lateral direction an image of the capsule medical apparatus 10 that is floating in the liquid 2 in the container 3. FIG. 14 is a schematic diagram showing an example of an actual image of the capsule medical apparatus that is floating in the liquid, which is taken in the lateral direction. The imaging unit 34 takes (acquires) in the lateral direction an actual image 106 while illuminating the capsule medical apparatus 10 that is floating in the liquid 2. The actual image 106 that is taken by the imaging unit 34 includes as an object the capsule medical apparatus 10 that is floating in the liquid 2, the liquid level 2a of the liquid 2, and a boundary portion B2 of the capsule medical apparatus 10. The boundary portion B2 of the capsule medical apparatus 10 is an external surface of a dome-shaped top portion of the capsule medical apparatus 10 that is vertical in the liquid 2. When the protruding portion 10a of the capsule medical apparatus 10 protrudes upward from the liquid level 2a as represented in FIG. 14, the boundary portion B2 is a boundary portion between the exterior of the capsule medical apparatus 10 and the atmosphere. The imaging unit 34 transmits an image signal of the actual image 106 to the control unit 38.

The control unit 38 has an imaging control function for controlling operations of the imaging unit 34 instead of the imaging control function of the imaging unit 24 according to the second embodiment. Specifically, the control unit 38 controls the imaging unit 34 to take the actual image 106 of the capsule medical apparatus 10 in the liquid 2 based on instruction information that is input by the input unit 5, and acquires an image signal of the actual image 106 from the imaging unit 34. The control unit 38 stores in the storage unit 7 or displays on the display unit 6 the actual image 106 of the capsule medical apparatus 10 that is taken by the imaging unit 34 instead of the actual image 105 of the capsule medical apparatus 10.

The control unit 38 includes an image processor 38b instead of the image processor 28b of the floatation-volume adequacy determining system 21 according to the second embodiment, and an adequacy determining unit 38c instead of the adequacy determining unit 28c. Other functions of the control unit 38 are same as those of the control unit 28 of the floatation-volume adequacy determining system 21 according to the second embodiment.

The image processor 38b performs predetermined image processing on the image signal that is acquired from the imaging unit 34, and generates the actual image 106 (see FIG. 14) of the capsule medical apparatus 10 that is taken by the imaging unit 34. The image processor 38b sets an adequate range CR2 of the floatation volume of the capsule medical apparatus 10 in the liquid 2, and generates a determination reference image that represents the adequate range CR2. In this case, the image processor 38b converts the upper-limit protrusion amount $X_{AU}$ and the lower-limit protrusion amount $X_{AL}$, which are calculated by the arithmetic processor 8a, to pixels of the actual image 106 and sets, as the adequate range CR2 of the floatation volume, a pixel area between the upper-limit protrusion amount $X_{AU}$ and the lower-limit protrusion amount $X_{AL}$. The actual image 106 or the determination reference image that is processed by the image processor 38b is stored in the storage unit 7 under the control of the control unit 38 and read by the control unit 38 appropriately.

In the third embodiment, it suffices that the arithmetic processor 8a finally calculate the upper-limit protrusion amount $X_{AU}$ and the lower-limit protrusion amount $X_{AL}$ of protrusion of the capsule medical apparatus 10 from the liquid level 2a of the liquid 2 based on the physical information about the capsule medical apparatus 10. In other words, the arithmetic processor 8a of the control unit 38 does not need to calculate an upper-limit radius $r_{AU}$ and a lower-limit radius $r_{AL}$ of the boundary portion B2 between the exterior of the capsule medical apparatus 10 and the liquid level 2a.

The adequacy determining unit 38c compares with each other the determination reference image that is generated by the image processor 38b and the actual image 106 of the capsule medical apparatus 10 that is taken by the imaging unit 34. Based on the result of the comparison, the adequacy determining unit 38c determines whether the floatation volume of the capsule medical apparatus 10 in the liquid 2 is adequate. Specifically, the adequacy determining unit 38c compares with each other the adequate range CR2 in the determination reference image and the boundary portion B2 in the actual image 106. When the boundary portion B2 is within the adequate range CR2, the adequacy determining unit 38c determines that the relative position of the boundary portion B2 to the liquid level 2a, i.e., the floatation volume of the capsule medical apparatus 10, is adequate. In contrast, when the boundary portion B2 is out of the adequate range CR2, the adequacy determining unit 38c determines that the floatation volume of the capsule medical apparatus 10 is inadequate.

Figure 15:
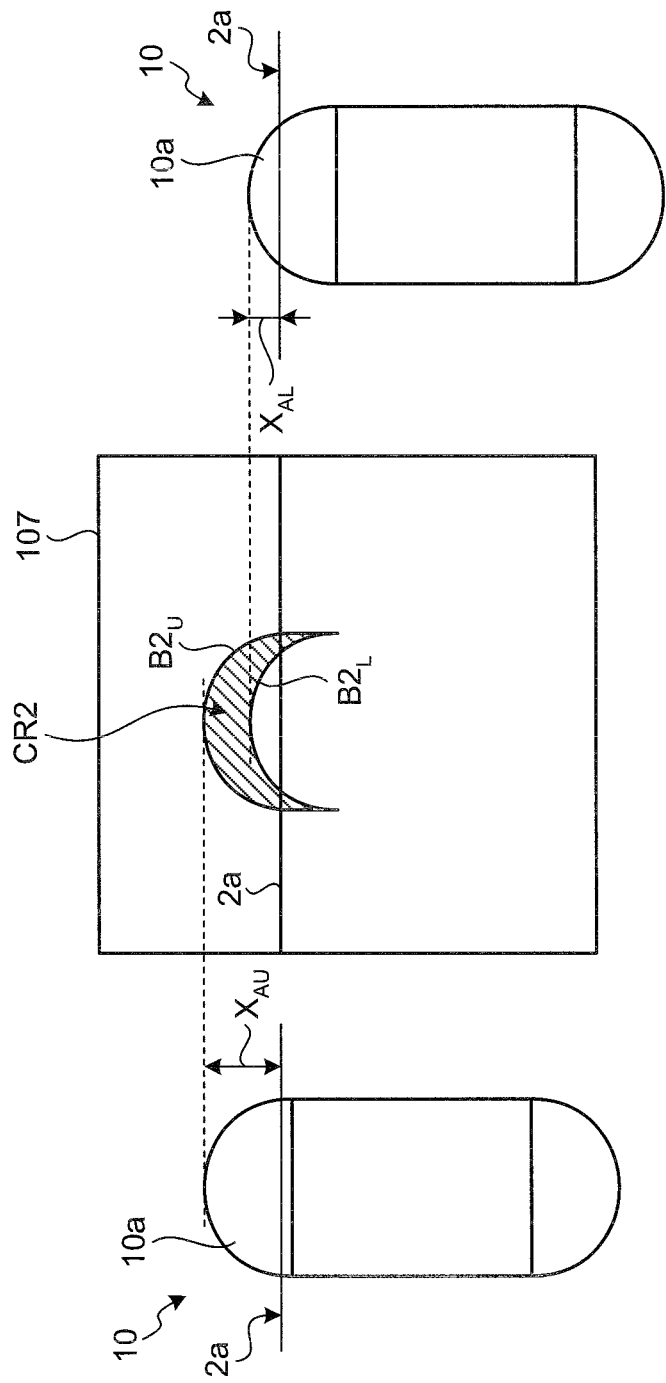
FIG. 15 is a schematic diagram explaining setting of an adequate range of a floatation volume of a capsule medical apparatus according to the third embodiment.
Figure 16:
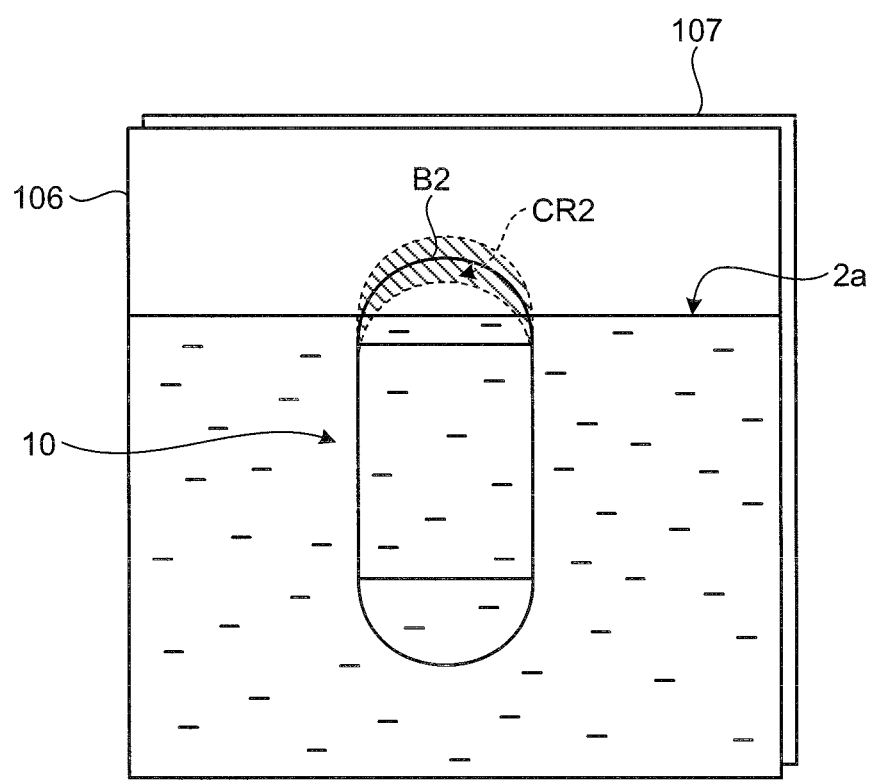
FIG. 16 is a schematic diagram explaining a process of determining whether the floatation volume of the capsule medical apparatus according to the third embodiment is adequate.

The floatation-volume adequacy determining method and operations of the floatation-volume adequacy determining system 31 according to the third embodiment of the present invention are described below. FIG. 15 is a schematic diagram explaining setting of the adequate range of the floatation volume of the capsule medical apparatus according to the third embodiment. FIG. 16 is a schematic diagram explaining a process of determining whether the floatation volume of the capsule medical apparatus is adequate in the third embodiment.

The floatation-volume adequacy determining method and operations of the floatation-volume adequacy determining system 31 according to the third embodiment are different from those of the second embodiment in that the actual image 106 of the capsule medical apparatus 10 that is floating in the liquid 2 is taken in the lateral direction; that the adequate range CR2 of the floatation volume of the capsule medical apparatus 10 is set; and that it is determined whether the floatation volume of the capsule medical apparatus 10 is adequate, using the actual image 106. Other operations and methods including the preparation operation are same as those of the second embodiment. In other words, the control unit 38 of the floatation-volume adequacy determining system 31 performs a procedure approximately same as that of steps S201 to S205 represented in FIG. 12.

At step S201, the control unit 38 controls the imaging unit 34 based on instruction information that is input by the input unit 5. The imaging unit 34 takes in the lateral direction an image of the capsule medical apparatus 10 in the liquid 2 based on the control of the control unit 38, and transmits an image signal of the actual image 106 of the capsule medical apparatus 10 to the control unit 38. The control unit 38 acquires the actual image 106 of the capsule medical apparatus 10 from the imaging unit 34.

At step S202, the arithmetic processor 8a calculates the upper-limit protrusion amount $X_{AU}$ and the lower-limit protrusion amount $X_{AL}$ of the capsule medical apparatus 10 from the liquid level 2a based on the above-described Equations (1) to (3). Using the upper-limit protrusion amount $X_{AU}$ and the lower-limit protrusion amount $X_{AL}$, which are calculated by the arithmetic processor 8a, the image processor 38b sets the adequate range CR2 of the floatation volume of the capsule medical apparatus 10 in the liquid 2. Specifically, the image processor 38b converts the upper-limit protrusion amount $X_{AU}$ and the lower-limit protrusion amount $X_{AL}$ to pixels that are displayed by the display unit 6 and adjusted to the actual image 106 of the capsule medical apparatus 10 that is taken by the imaging unit 34. As represented in FIG. 15, the image processor 38b then generates a determination reference image 107 including an upper-limit boundary portion $B2_U$ that corresponds to the upper limit of the boundary portion B2 (i.e., the upper-limit protrusion amount $X_{AU}$) and a lower-limit boundary portion $B2_L$ that corresponds to the lower limit of the boundary portion B2 (i.e., the lower-limit protrusion amount $X_{AL}$). In the determination reference image 107, the liquid level 2a of the liquid 2, in which the capsule medical apparatus 10 floats, is drawn.

The upper-limit boundary portion $B2_U$ is an upper limit within a predetermined range determined as a relative position of the boundary portion B2 of the capsule medical apparatus 10 relative to the liquid level 2a. The lower-limit boundary portion $B2_L$ is a lower limit within a predetermined range determined as a relative position of the boundary portion B2 of the capsule medical apparatus 10 relative to the liquid level 2a. As represented by a shaded portion in FIG. 15, the image processor 38b sets a pixel area between the upper-limit boundary portion $B2_U$ and the lower-limit boundary portion $B2_L$ as the adequate range CR2 of the floatation volume of the capsule medical apparatus 10 in the liquid 2. The determination reference image 107 that represents the adequate range CR2 is stored in the storage unit 7 based on the control of the control unit 38 and read by the control unit 38 appropriately.

At step S203, the control unit 38 determines whether the floatation volume of the capsule medical apparatus 10 in the liquid 2 is adequate, using the actual image 106 of the capsule medical apparatus 10 that is taken in the lateral direction by the imaging unit 34, instead of the actual image 105 taken from above. As represented in FIG. 16, the adequacy determining unit 38c matches the position of the liquid level 2a of the actual image 106 with the position of the liquid level 2a of the determination reference image 107, and compares with each other the boundary portion B2 in the actual image 106 and the adequate range CR2 in the determination reference image 107. When the boundary portion B2 is within the adequate range CR2, the adequacy determining unit 38c determines that the floatation volume of the capsule medical apparatus 10 in the liquid 2 is adequate. When the boundary portion B2 is out of the adequate range CR2, the adequacy determining unit 38c determines that the floatation volume of the capsule medical apparatus 10 is inadequate. In the case of FIG. 16, because the boundary portion B2 is positioned within the adequate range CR2, it is determined that the floatation volume of the capsule medical apparatus 10 is adequate.

At step S204, the control unit 38 controls the display unit 6 to display a comparison image between the boundary portion B2 of the capsule medical apparatus 10 and the adequate range CR2 of the floatation volume. The control unit 38 controls the display unit 6 to display the adequate range CR2 of the floatation volume of the capsule medical apparatus 10 and the actual image 106, which is acquired from the imaging unit 34, such that the adequate range CR2 is superimposed on the actual image 106. Based on the control of the control unit 38, the display unit 6 outputs and displays the comparison image with which the boundary portion B2 and the adequate range CR2 of the floatation volume can be visually compared with each other. In the third embodiment, the comparison image is generated by the image processor 38b by superimposing the determination reference image 107 on the actual image 106.

In the third embodiment, by visually recognizing the comparison image that is displayed on the display unit 6, the user can easily compare with each other the boundary portion B2 of the capsule medical apparatus 10 and the adequate range CR2 of the floatation volume. Accordingly, the user can easily determine whether the floatation volume of the capsule medical apparatus 10 to be examined is adequate. When the boundary portion B2 deviates to an upper side of the adequate range CR2 in the comparison image, the user can know that the capsule medical apparatus 10 is inadequate because it floats too much. In contrast, when the boundary portion B2 deviates to a lower side of the adequate range CR2, the user can know that the capsule medical apparatus 10 is inadequate because it sinks too much.

As described above, in the third embodiment, the actual image including the liquid level and the capsule medical apparatus that is floating in the liquid is taken in the lateral direction, and the adequate range of the floatation volume of the capsule medical apparatus to be examined is set in accordance with the actual image. Other aspects of the configuration are same as those of the second embodiment. Accordingly, the effects and functions same as those of the second embodiment can be achieved and it can be directly determined whether the amount of protrusion of the capsule medical apparatus from the liquid level (i.e., the floatation volume) is adequate. As a result, the floatation-volume adequacy determining system and the floatation-volume adequacy determining method with which arithmetic processing for determining the adequacy can be simplified can be provided.

In the first to third embodiments, the comparison image between the boundary portion of the capsule medical apparatus to be examined and the adequate range of the floatation volume is displayed on the display unit. Alternatively, the floatation-volume adequacy determining system that has the function for determining whether the floatation volume of the capsule medical apparatus is adequate may display a result of determining whether the floatation volume of the capsule medical apparatus is adequate without displaying the comparison image. In other words, step S104 from the procedure of steps S101 to S105 may not be performed and step S204 from the procedure of steps S201 to S205 may not be performed.

In the first to third embodiments, the floatation-volume adequacy determining systems and the floatation-volume adequacy determining methods, in which it is determined whether the floatation volume of the capsule medical apparatus in the liquid is adequate and the result of determining whether the floatation volume of the capsule medical apparatus is adequate is displayed on the display unit, are exemplarily represented. Alternatively, in the floatation-volume adequacy determining system and the floatation-volume adequacy determining method, the comparison image with which the boundary portion of the capsule medical apparatus to be examined and the adequate range of the floatation volume can be visually compared with each other may be displayed on the display unit without determining whether the floatation volume of the capsule medical apparatus is adequate.

Specifically, in the floatation-volume adequacy determining system and the floatation-volume adequacy determining method according to the first embodiment, the processes at steps S101, S102, and S104 of the procedure of steps S101 to S105 may be sequentially performed without steps S103 and S105. In this case, the floatation-volume adequacy determining system according to the first embodiment may not include the adequacy determining unit. Similarly, in the floatation-volume adequacy determining systems and the floatation-volume adequacy determining methods according to the second and third embodiments, the processes at steps S201, S202, and S204 of the procedure of steps S201 to S205 may be sequentially performed without steps S203 and S205. In this case, the floatation-volume adequacy determining system according to the second and third embodiments may not include the adequacy determining unit.

In the first to third embodiment, the result of determining whether the floatation volume of the capsule medical apparatus in the liquid is adequate is displayed on the display unit. Alternatively, the result of determining whether the floatation volume is adequate may be output as sound information, such as voice or beep sound. In this case, the floatation-volume adequacy determining systems according to the first to third embodiments each may include a sound output unit, such as a speaker, and output sound information, such as voice or beep sound, that represents the result of determining whether the floatation volume is adequate to notify the user of the result of determining whether the floatation volume is adequate.

In the first to third embodiments, the capsule medical apparatuses that erect while floating in the liquid are exemplarily represented. The capsule medical apparatuses may not necessarily erect. Alternatively, for example, the longitudinal direction of the capsule medical apparatuses may be approximately parallel to the horizontal direction, i.e., the capsule medical apparatuses may be horizontal, or the longitudinal direction of the capsule medical apparatuses may be oblique to the vertical direction.

In the second and third embodiments, the container 3 whose inner diameter is larger than the outer diameter of the capsule medical apparatus to be examined is used. Alternatively, a container whose inner diameter is slightly larger than the outer diameter of the capsule medical apparatus may be used to prevent the capsule medical apparatus, which is floating in the liquid in the container, from moving by the inner wall of the container. In this case, the shape of the container is not limited to a cylindrical shape, and it may be a desirable shape, such as a rectangular shape. Alternatively, a magnet may be arranged near the container 3 to prevent the capsule medical apparatus in the liquid from moving by a magnetic field of the magnet. In both cases, by preventing the capsule medical apparatus that is floating in the liquid from moving, an actual image that includes the capsule medical apparatus as an object can be easily taken.

In the first to third embodiments, binocular capsule medical apparatuses each of which includes two imaging units are exemplarily represented. Alternatively, the capsule medical apparatus to be examined may be a monocular capsule medical apparatus that incorporates a single imaging unit or + may be a multinocular capsule medical apparatus that incorporates three or more imaging units. The capsule medical apparatuses to be examined in the second and third embodiments may be capsule medical apparatuses with no imaging unit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A system for determining whether a floatation volume of a capsule medical apparatus floating in a liquid is adequate, the system comprising:
   an image acquiring unit that acquires an actual image of the capsule medical apparatus that is floating in the liquid, the actual image including a boundary portion between a level of the liquid and an exterior of the capsule medical apparatus;
   an image processing unit that generates a determination reference image that represents a predetermined floatation volume range of the capsule medical apparatus considered to be adequate; and
   an adequacy determining unit that compares the determination reference image with the actual image and determines whether the floatation volume of the capsule medical apparatus is adequate based on the result of the comparison.

2. The system according to claim 1, further comprising an output unit that outputs a result of the determination of whether the floatation volume of the capsule medical apparatus is adequate to a display unit for displaying the result.

3. The system according to claim 1, wherein:
   the actual image is an image that is taken by the capsule medical apparatus that is floating in the liquid, and
   the image acquiring unit comprises a receiving unit that receives the actual image that is wirelessly transmitted by the capsule medical apparatus.

4. The system according to claim 1, wherein the image acquiring unit comprises an imaging unit that takes the actual image.

5. The system according to claim 4, wherein the imaging unit takes the actual image from above the capsule medical apparatus.

6. The system according to claim 4, wherein the imaging unit takes the actual image in a lateral direction.

7. The system according to claim 1, wherein the image acquiring unit acquires the actual image that includes the boundary portion between the level of the liquid, the liquid being colored, and the exterior of the capsule medical apparatus.

8. A system comprising:
   an image acquiring unit that acquires an actual image of a capsule medical apparatus that is floating in a liquid, the actual image including a boundary portion between a level of the liquid and an exterior of the capsule medical apparatus;
   a display unit that displays the actual image; and
   a control unit that sets a predetermined floatation volume range of the capsule medical apparatus considered to be adequate adjusted to a display scale of the display unit and causes the display unit to display the predetermined floatation volume range and the actual image such that the predetermined floatation volume range is superimposed on the actual image.

9. The system according to claim 8, wherein:
the actual image is an image that is taken by the capsule medical apparatus that is floating in the liquid, and
the image acquiring unit comprises a receiving unit that receives the actual image that is wirelessly transmitted by the capsule medical apparatus.

10. The system according to claim 8, wherein the image acquiring unit comprises an imaging unit that takes the actual image.

11. The system according to claim 10, wherein the imaging unit takes the actual image from above the capsule medical apparatus.

12. The system according to claim 10, wherein the imaging unit takes the actual image in a lateral direction.

13. The system according to claim 8, wherein the image acquiring unit acquires the actual image that includes the boundary portion between the level of the liquid, the liquid being colored, and the exterior of the capsule medical apparatus.

14. A method for determining whether a floatation volume of a capsule medical apparatus floating in a liquid is adequate, the method comprising:
acquiring an actual image of the capsule medical apparatus that is floating in the liquid, the actual image including a boundary portion between a level of the liquid and an exterior of the capsule medical apparatus;
generating by a processor a determination reference image that represents a predetermined floatation volume range of the capsule medical apparatus considered to be adequate;
comparing by the processor the determination reference image with the actual image; and
determining by the processor whether the floatation volume of the capsule medical apparatus is adequate based on the result of the comparison.

15. The method according to claim 14, further comprising outputting a result of the determination of whether the floatation volume of the capsule medical apparatus is adequate to a display unit for displaying the result.

16. The method according to claim 14, wherein the acquiring of the actual image includes:
the capsule medical apparatus that is floating in the liquid taking the actual image,
the capsule medical apparatus wirelessly transmitting the actual image, and
a receiving unit receiving the actual image that is wirelessly transmitted by the capsule medical apparatus.

17. The method according to claim 14, wherein the acquiring of the actual image includes an imaging unit that is separate from the capsule medical apparatus taking the actual image of the capsule medical apparatus floating in the liquid.

18. The method according to claim 17, wherein the acquiring of the actual image includes taking the actual image from above the capsule medical apparatus.

19. The method according to claim 17, wherein the acquiring of the actual image includes taking the actual image in a lateral direction.

20. A method comprising:
acquiring an actual image of a capsule medical apparatus that is floating in a liquid, the actual image including a boundary portion between a level of the liquid and an exterior of the capsule medical apparatus;
setting by a processor a predetermined floatation volume range of the capsule medical apparatus considered to be adequate adjusted to a display scale of a display unit; and
controlling by the processor to display on the display unit the predetermined floatation volume range superimposed on the actual image.

21. The method according to claim 20, wherein the acquiring of the actual image includes:
the capsule medical apparatus that is floating in the liquid taking the actual image,
the capsule medical apparatus wirelessly transmitting the actual image, and
a receiving unit receiving the actual image that is wirelessly transmitted by the capsule medical apparatus.

22. The method according to claim 20, wherein the acquiring of the actual image includes an imaging unit that is separate from the capsule medical apparatus taking the actual image of the capsule medical apparatus floating in the liquid.

23. The method according to claim 22, wherein the acquiring of the actual image includes taking the actual image from above the capsule medical apparatus.

24. The method according to claim 22, wherein the acquiring of the actual image includes taking the actual image in a lateral direction.

* * * * *